(12) United States Patent
Almena-Perea et al.

(10) Patent No.: US 8,629,134 B2
(45) Date of Patent: Jan. 14, 2014

(54) ENANTIOSELECTIVE SYNTHESIS OF 6-AMINO-7-HYDROXY-4,5,6,7-TETRAHYDRO-IMIDAZO[4,5,1-JK][1]-BENZAZEPIN-2[1H]-ONE AND ZILPATEROL

(75) Inventors: Juan Jose Almena-Perea, Hanau (DE); Monika Brink, Schwabenheim (DE); Gerhard Geiβ, Hanau (DE); Renat Kadyrov, Hanau (DE); Thorsten Meyer, Schwabenheim (DE)

(73) Assignee: Intervet International B.V., Boxmeer (NL)

( * ) Notice: Subject to any disclaimer, the term of this patent is extended or adjusted under 35 U.S.C. 154(b) by 684 days.

(21) Appl. No.: 12/525,222

(22) PCT Filed: Jan. 31, 2008

(86) PCT No.: PCT/EP2008/051206
§ 371 (c)(1),
(2), (4) Date: Jul. 30, 2009

(87) PCT Pub. No.: WO2008/092924
PCT Pub. Date: Aug. 7, 2008

(65) Prior Publication Data
US 2010/0173892 A1    Jul. 8, 2010

Related U.S. Application Data

(60) Provisional application No. 60/899,336, filed on Feb. 1, 2007.

(51) Int. Cl.
*A61P 43/00* (2006.01)
*A61K 31/55* (2006.01)
*C07D 487/06* (2006.01)

(52) U.S. Cl.
USPC ..................... 514/214.02; 540/579

(58) Field of Classification Search
USPC ..................... 514/214.02; 540/579
See application file for complete search history.

(56) References Cited

U.S. PATENT DOCUMENTS

| 4,585,770 | A  | 4/1986  | Frechet et al. |
| 4,900,735 | A  | 2/1990  | Grandadam |
| 5,731,028 | A  | 3/1998  | Chevremont et al. |
| 6,348,620 | B1 | 2/2002  | Knochel et al. |
| 2006/0241315 | A1 | 10/2006 | Spindler et al. |
| 2008/0103130 | A1 | 5/2008  | Boyle et al. |
| 2008/0267942 | A1 | 10/2008 | Boyle et al. |

FOREIGN PATENT DOCUMENTS

| EP | 197188 A1 | 5/1989 |
| JP | S59130289 A | 7/1984 |
| JP | 1993004948 A | 1/1993 |
| JP | 2915161 | 7/1999 |
| JP | 2001106664 A | 4/2001 |
| WO | 2008006828 A1 | 1/2008 |
| WO | WO 2008/044127 A1 | 4/2008 |
| WO | WO 2008/092924 A1 | 8/2008 |

OTHER PUBLICATIONS

Invention Data, Thursday Aug. 26, 2010.
PCT International Search Report, PCT/EP2008/051206, dated Jun. 12, 2008.
Rebstock et al., Chloromycetin (Chloramphenicol[1]). Related Compounds Having Alkyl Side Chain Variations, 1951

*Primary Examiner* — Brenda Coleman

(57) ABSTRACT

This invention relates to a process for the hydrogenation of a ketooxime to selectively form an aminoalcohol stereoisomer, and, in particular, to a process for the hydrogenation of 4,5-dihydro-imidazo[4,5,1-jk][1]benzazepin-2,6,7[1H]-trione-6-oxime or a salt thereof to selectively form a stereoisomer of 6-amino-7-hydroxy-4,5,6,7-tetrahydro-imidazo[4,5,1-jk][1]-benzazepin-2[1H]-one or a salt thereof. This invention also relates to the use of the 6-amino-7-hydroxy-4,5,6,7-tetrahydro-imidazo[4,5,1-jk][1]-benzazepin-2[1H]-one hydrogenation product or a salt thereof to selectively make a stereoisomer of zilpaterol or a salt thereof, as well as the use of such a zilpaterol stereoisomer or salt in methods of treatment and medicaments for animals.

29 Claims, No Drawings

ENANTIOSELECTIVE SYNTHESIS OF 6-AMINO-7-HYDROXY-4,5,6,7-TETRAHYDRO-IMIDAZO[4,5,1-JK][1]-BENZAZEPIN-2[1H]-ONE AND ZILPATEROL

CROSS-REFERENCE TO RELATED PATENT APPLICATION

This application is the United States national stage application of International Application No. PCT/EP2008/051206 filed Jan. 31, 2008, which claims priority from U.S. Provisional application No. 60/899,336, filed on Feb. 1, 2007.

FIELD OF THE INVENTION

This invention relates to a process for the hydrogenation of a ketooxime to selectively form an aminoalcohol stereoisomer, and, in particular, to a process for the hydrogenation of 4,5-dihydro-imidazo[4,5,1-jk][1]benzazepin-2,6,7 [1H]-trione-6-oxime or a salt thereof to selectively form a stereoisomer of 6-amino-7-hydroxy-4,5,6,7-tetrahydro-imidazo[4,5,1-jk][1]-benzazepin-2[1H]-one or a salt thereof. This invention also relates to the use of the 6-amino-7-hydroxy-4,5,6,7-tetrahydro-imidazo[4,5,1-jk][1]-benzazepin-2[1H]-one hydrogenation product or a salt thereof to selectively make a stereoisomer of zilpaterol or a salt thereof, as well as the use of such a zilpaterol stereoisomer or salt in methods of treatment and medicaments for animals.

BACKGROUND OF THE INVENTION

Zilpaterol is a known adrenergic β-2 agonist having the following structure:

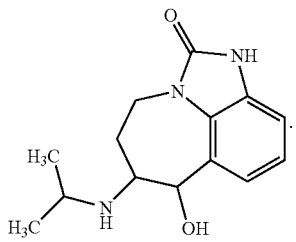 [SMILES: CC(C)NC1CCn2c(=O)[nH]c3cccc(c32)C1O]

The IUPAC name for zilpaterol is 4,5,6,7-tetrahydro-7-hydroxy-6-(isopropylamino) imidazo[4,5,1-jk]-[1]benzazepin-2(1H)-one. The Chemical Abstracts name for zilpaterol is 4,5,6,7-tetrahydro-7-hydroxy-6-[(1-methyl-ethyl)amino]-imidazo[4,5,1-jk][1]benzazepin-2(1H)-one.

The generic structure encompassing zilpaterol has two chiral atoms:

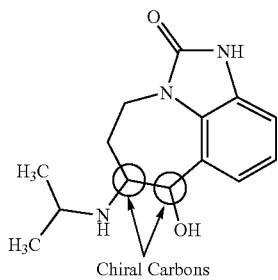 [SMILES: CC(C)NC1CCn2c(=O)[nH]c3cccc(c32)C1O]

Consequently, zilpaterol has four stereoisomers. These stereoisomers may be identified as "(6R,7R)," "(6R,7S)," "(6S, 7R)," and "(6S,7S)." Racemic trans zilpaterol (i.e., a mixture of the (6R,7R) and (6S,7S) stereoisomers) has been identified in the literature as "RU42173." These trans stereoisomers have the following structures:

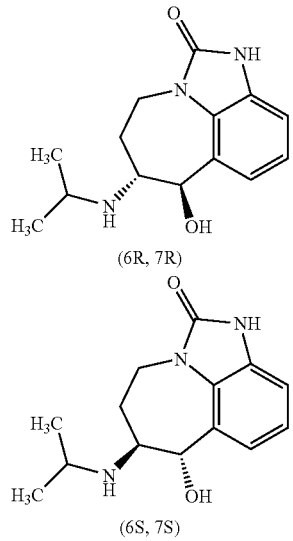

It is well known that zilpaterol, various zilpaterol derivatives, and various pharmaceutically acceptable acid addition salts of zilpaterol and its derivatives may, for example, be used to increase the rate of weight gain, improve feed efficiency (i.e., decrease the amount of feed per amount of weight gain), and/or increase carcass leanness (i.e., increase protein content in carcass soft tissue) in livestock, poultry, and/or fish. In U.S. Pat. No. 4,900,735, for example, Grandadam describes zootechnical compositions of racemic trans zilpaterol and salts thereof that may be used to increase the weight and meat quality of warm-blooded animals, including cattle, pigs, sheep, and poultry. And U.S. Pat. No. 7,207,289 describes using ionophore/macrolide/zilpaterol dosing regimens to increase beef production, reduce feed intake while maintaining beef production, and reduce incidences of liver abscess in cattle.

Methods for making zilpaterol are known in the art. For example, in U.S. Pat. No. 4,585,770, Fréchet et al. discuss compounds encompassed by a genus characterized as 6-amino-7-hydroxy-4,5,6,7-tetrahydro-imidazo[4,5,1-jk][1]-benzazepin-2[1H]-one derivatives and pharmaceutically acceptable acid addition salts thereof. The derivatives correspond in structure to the following formula:

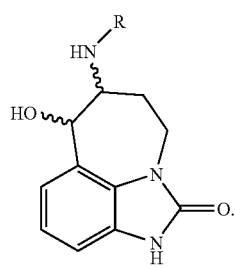

Here, R can be various substituents, and the wavy lines indicate that the bonds to the 6-amino and 7-OH groups have the trans configuration. This genus encompasses racemic trans zilpaterol when R is isopropyl.

The methods reported in U.S. Pat. No. 4,585,770 use 4,5-dihydro-imidazo[4,5,1-jk][1]benzazepin-2,6,7[1H]-trione-6-oxime as an intermediate. This compound corresponds in structure to Formula (I):

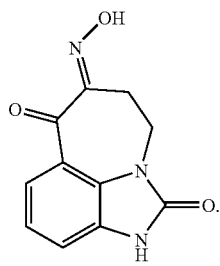

(I)

As indicated in U.S. Pat. No. 4,585,770, 4,5-dihydro-imidazo[4,5,1-jk][1]benzazepin-2,6,7[1H]-trione-6-oxime may be formed from starting materials that have been long known in the art. U.S. Pat. No. 4,585,770 illustrates the use of two such starting materials. In both examples, the starting materials are used to form 5,6-dihydro-imidazo[4,5,1-jk][1]benzazepin-2,7-[1H,4H]-dione, which, in turn, may be used to make 4,5-dihydro-imidazo[4,5,1-jk][1]benzazepin-2,6,7 [1H]-trione-6-oxime.

In one of the examples in U.S. Pat. No. 4,585,770, the starting material is 1,3-dihydro-1-(1-methylethenyl)-2H-benzimidazol-2-one, which is described in *J. Chem. Soc. Perkins*, p. 261 (1982):

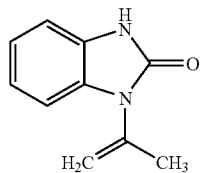

1,3-dihydro-1-(1-methylethenyl)-2H-benzimidazol-2-one

U.S. Pat. No. 4,585,770 indicates that 1,3-dihydro-1-(1-methylethenyl)-2H-benzimidazol-2-one may be reacted with an alkyl 4-halobutyrate (i.e., $R^A$—$(CH_2)_3$—$COOR^B$ (wherein $R^A$ is Cl, Br, or I; and $R^B$ is $C_1$-$C_4$-alkyl), such as methyl or ethyl 4-bromobutyrate) and a base (e.g., an alkali metal) to form a butanoate, which, in turn may be hydrolyzed with an acid (e.g., $H_2SO_4$) in an alkanol (e.g., methanol or ethanol) to remove the methylethenyl substituent. The hydrolysis product then may be subjected to saponification by reacting it with a base (e.g., NaOH or KOH) in an alkanol to form a carboxylic acid. Subsequently, the carboxylic-acid-terminated side chain may be cyclized to form 5,6-dihydro-imidazo[4,5,1-jk][1]benzazepin-2,7-[1H,4H]-dione by reacting the carboxylic acid with thionyl chloride to obtain a chloride, and then treating the chloride with a Lewis acid (e.g., aluminum chloride) in an organic solvent (e.g., methylene chloride or dichloroethane):

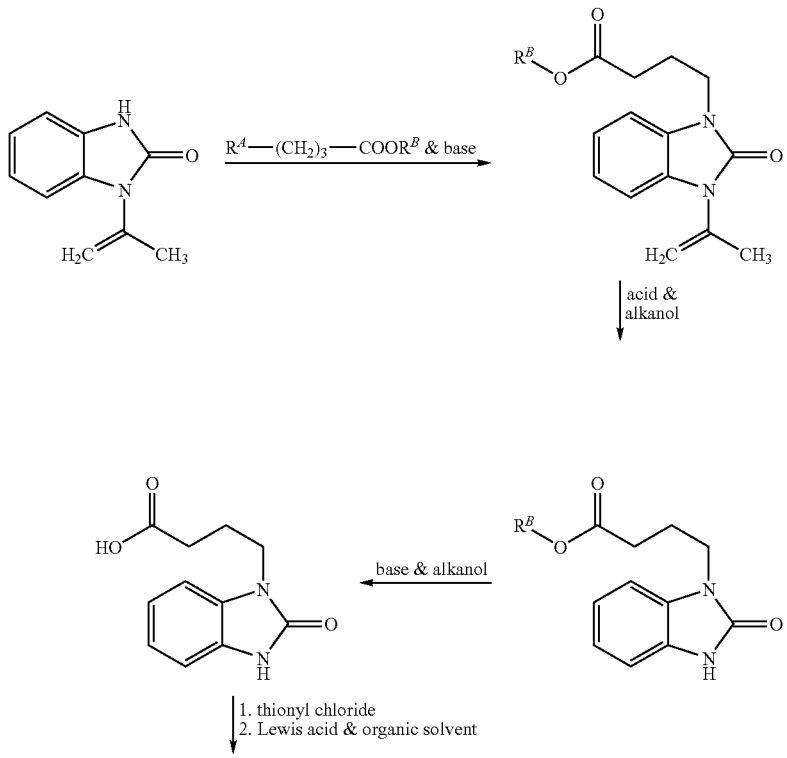

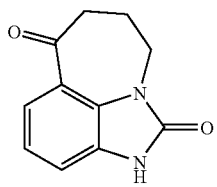

dihydro-imidazo[4,5,1-jk][1]
benzazepin-2,7,-91H,4H]-dione

See U.S. Pat. No. 4,585,770, col. 4, line 3 to col. 5, line 14; and Example 14, col. 12, lines 1-68.

In another example in U.S. Pat. No. 4,585,770, the starting material is 1,3-dihydro-1-benzyl-2H-benzimidazol-2-one, which is described in *Helv.*, Vol 44, p. 1278 (1961):

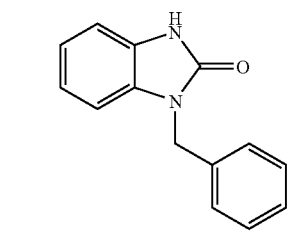

1,3-dihydro-1-benzyl-2H-benzimidazol-2-one

U.S. Pat. No. 4,585,770 indicates that the 1,3-dihydro-1-benzyl-2H-benzimidazol-2-one may be reacted with ethyl 4-bromobutyrate and sodium hydride to form 1,3-dihydro-2-oxo-3-benzyl-1H-benzimidazol-1-butanoate, which, in turn may be subjected to saponification by reacting it with methanolic NaOH to form 1,3-dihydro-2-oxo-3-benzyl-1H-benzimidazol-1-butanoic acid. The butanoic acid side chain may then be cyclized by reacting the 1,3-dihydro-2-oxo-3-benzyl-1H-benzimidazol-1-butanoic acid with thionyl chloride to obtain a chloride, and then treating the chloride with aluminum chloride in dichloroethane. The cyclized product, in turn, may be hydrolyzed using o-phosphoric acid in phenol to form 5,6-dihydro-imidazo[4,5,1-jk][1]benzazepin-2,7-[1H,4H]-dione. See U.S. Pat. No. 4,585,770, Example 1, Steps A-D, col. 6, line 10 to col. 7, line 35.

Using the methods reported in U.S. Pat. No. 4,585,770, 5,6-dihydro-imidazo[4,5,1-jk][1]benzazepin-2,7-[1H,4H]-dione may be reacted with an alkyl nitrite (e.g., tert-butyl nitrite or isoamyl nitrite), in the presence of a base or acid (e.g., HCl), to form 4,5-dihydro-imidazo[4,5,1-jk][1]benzazepin-2,6,7[1H]-trione-6-oxime. The 4,5-dihydro-imidazo[4,5,1-jk][1]benzazepin-2,6,7[1H]-trione-6-oxime, in turn, is reduced via catalytic hydrogenation (with, for example, hydrogen in the presence of palladium on carbon) and/or sodium borohydride to form racemic trans 6-amino-7-hydroxy-4,5,6,7-tetrahydro-imidazo[4,5,1-jk][1]-benzazepin-2[1H]-one:

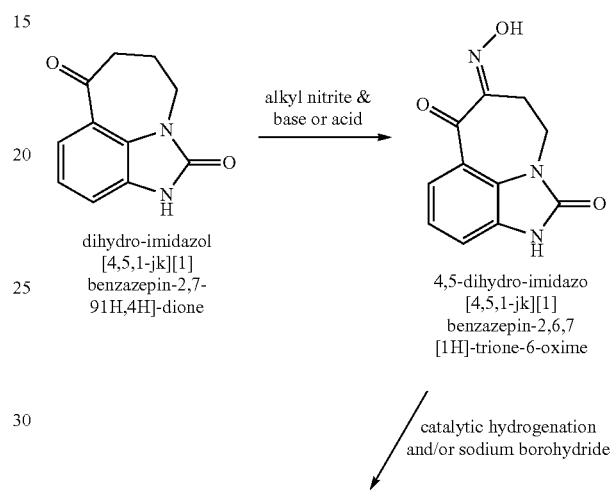

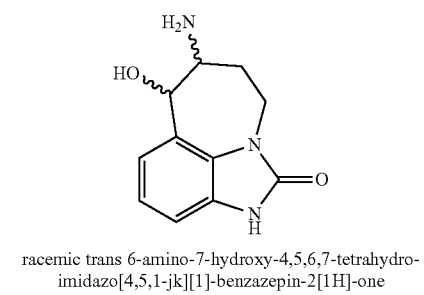

racemic trans 6-amino-7-hydroxy-4,5,6,7-tetrahydro-
imidazo[4,5,1-jk][1]-benzazepin-2[1H]-one In the illustrative example in U.S. Pat. No. 4,585,770, the 4,5-dihydro-imidazo[4,5,1-jk][1]benzazepin-2,6,7[1H]-trione-6-oxime is converted into racemic trans 6-amino-7-hydroxy-4,5,6,7-tetrahydro-imidazo[4,5,1-jk][1]-benzazepin-2 [1H]-one in two steps: the 4,5-dihydro-imidazo[4,5,1-jk][1]benzazepin-2,6,7 [1H]-trione-6-oxime is first reacted with $H_2$ in the presence of Pd carbon, and, then, after filtration, the hydrogenation product is reacted with sodium borohydride. See U.S. Pat. No. 4,585,770, col. 2, line 50 to col. 4, line 2; and Example 1, Steps E & F, col. 7, line 38 to col. 8, line 3.

U.S. Pat. No. 4,585,770 reports that the trans stereoisomers of 6-amino-7-hydroxy-4,5,6,7-tetrahydro-imidazo[4,5,1-jk][1]-benzazepin-2[1H]-one may be alkylated with acetone in the presence of a reducing agent (e.g., an alkali metal borohydride or cyanoborohydride, such as sodium cyanoborohydride) to form racemic trans zilpaterol:

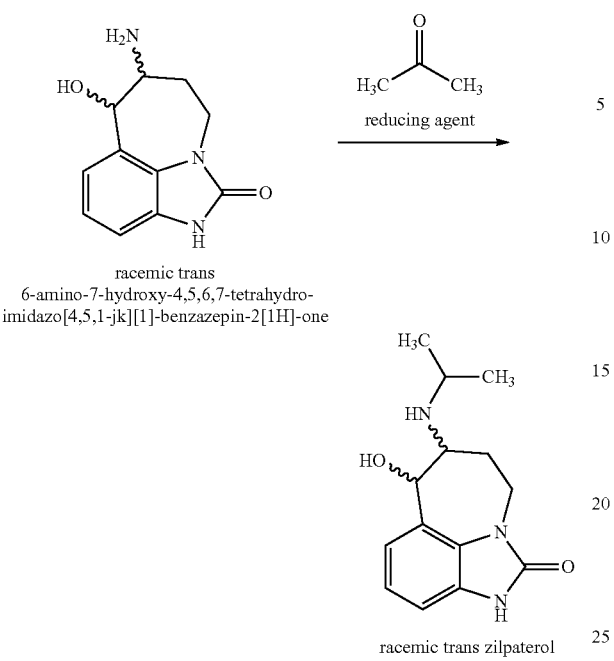

tively synthesizing one 6-amino-7-hydroxy-4,5,6,7-tetrahydro-imidazo[4,5,1-jk][1]-benzazepin-2[1H]-one or zilpaterol stereoisomer over all the other three respective stereoisomers. Int'l Patent Appl. PCT/EP2007/057036, for example, instead discusses separation techniques to isolate the trans(−) zilpaterol stereoisomer from racemic trans zilpaterol.

U.S. Pat. No. 6,284,925 discusses a genus of enantiomeric bisphosphine ligand complexes that reportedly may be used in enantioselective hydrogenations. The ligand complexes correspond in structure to the following formula:

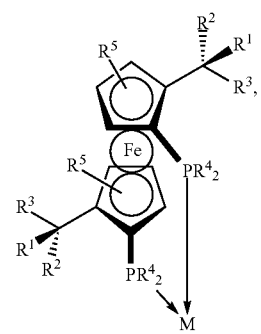

In U.S. Pat. Nos. 5,731,028 and 5,847,124, Chevremont et al. discuss crystallized anhydrous zilpaterol hydrochloride, and particularly crystallized anhydrous zilpaterol hydrochloride wherein less than 5% of the crystals have a size of less than 15 μm, and at least 95% of the crystals have a size of less than 250 μm. According to Chevremont et al., such crystals may be incorporated into animal feed to increase body weight and meat quality. Chevremont et al. provide methods for making such crystals, and discuss using the crystals to make animal premixes in which the crystals are secured to a corn cob support having a greater particle size. They also discuss monohydrate and trihydrate intermediates that can be useful in, for example, making the crystals.

There is an interest in processes that can be used to selectively make one stereoisomer of zilpaterol over the other three stereoisomers. There is particularly an interest in processes that can be used to selectively make one trans stereoisomer (i.e., the trans(−) stereoisomer) over the other three stereoisomers (i.e., over the other trans and both cis stereoisomers). It is contemplated that there may be benefits in using compositions that contain mostly (or only) one zilpaterol stereoisomer relative to racemic compositions or other compositions that contain more equivalent amounts of two or more stereoisomers. Such contemplated benefits may include, for example, greater efficacy, greater target selectivity, improved handling characteristics, fewer side effects, reduced drug tissue concentrations, and/or the ability to eliminate another stereoisomer having adverse side effects.

Applicants are unaware of any known process for selectively synthesizing one stereoisomer of either 6-amino-7-hydroxy-4,5,6,7-tetrahydro-imidazo[4,5,1-jk][1]-benzazepin-2[1H]-one or zilpaterol over all their other three respective stereoisomers.

There have been some discussions in the art relating to use of single-stereoisomer compositions of various adrenergic β-2 agonists. Such discussions may be found in, for example, U.S. Pat. No. 6,110,974; US Patent Appl. Publ. 2005/0113456; US Patent Appl. Publ. 2002/0132830, and Int'l Patent Appl. PCT/EP2007/057036 (filed Jul. 10, 2007). These discussions, however, provide no instruction for selecwherein $R^1$, $R^2$, $R^3$, $R^4$, and $R^5$ are selected from a range of substituents; and M is defined as "a metal atom or metal ion of the subgroup [B group] 8, e.g., Ni, Co, Rh, Ru, Ir, Pd, Re, or Pt." U.S. Pat. No. 6,248,925 illustrates the use of such ligand complexes for the enantioselective hydrogenation of the alkene in acetamido acrylates:

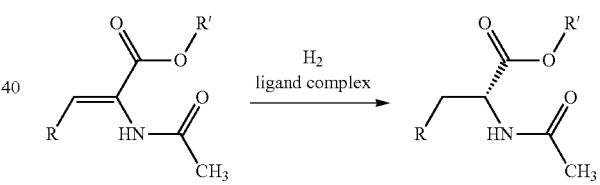

In these illustrations, R is hydrogen, phenyl, or 2-naphthyl; and R' is hydrogen or methyl. U.S. Pat. No. 6,248,925, however, does not discuss double-hydrogenations of a ketooxime to selectively make a stereoisomer of an amino alcohol.

U.S. Pat. No. 6,348,620 discusses enantioselective hydrogenations of ketoesters:

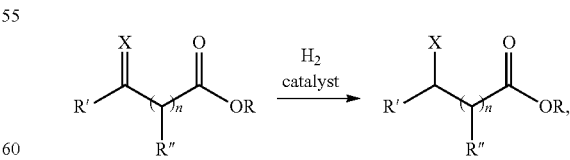

wherein X is O, CHR", NR", NNHR"; n is zero, 1, 2, or 3; and R, R', and R" are selected from a range of substituents. U.S. Pat. No. 6,348,620 reports that this hydrogenation may be catalyzed by bisphosphine ligand complexes corresponding in structure to the following formula:

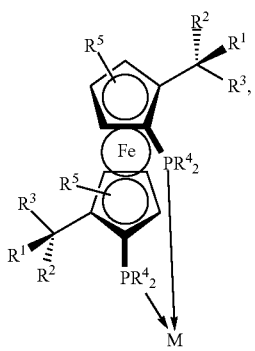

wherein $R^1$, $R^2$, $R^3$, $R^4$, and $R^5$ are selected from a range of substituents; and M is defined as "a metal atom or metal ion of the subgroup 7 or 8 such as, e.g., Co, Ni, Rh, Ru, Ir, Pd, Re, or Pt." U.S. Pat. No. 6,348,620 does not discuss double-hydrogenations of a ketooxime to selectively make a stereoisomer of an amino alcohol.

US Patent Appl. Publ. 2006/0241315 discusses a genus of enantiomeric bisphosphine ligands that reportedly may be used in complexes with transition group VIII metals for enantioselective hydrogenations. The ligands correspond in structure to the following formula:

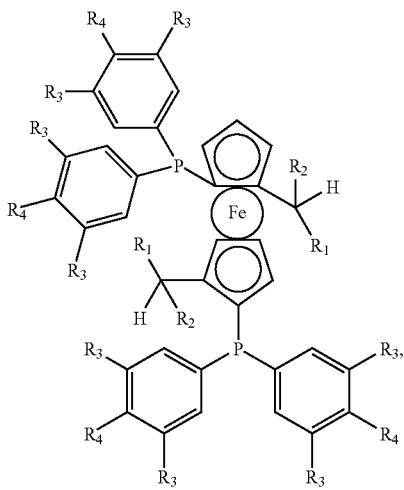

wherein $R^1$, $R^2$, $R^3$, and $R^4$ are selected from a range of substituents. US Patent Appl. Publ. 2006/0241315 focuses on and illustrates the use of such ligands for the enantioselective hydrogenation of alkenes. US Patent Appl. Publ. 2006/0241315, however, does not discuss double-hydrogenations of a ketooxime to selectively make a stereoisomer of an aminoalcohol.

Japanese Patent Ref. 2915161 discusses a process for preparing optically active aminoalcohols from ketooximes. It characterizes this process as a two-step process:

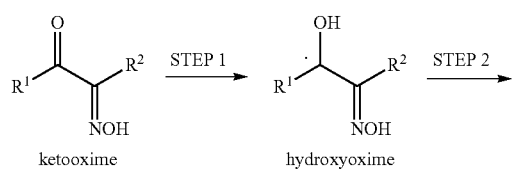

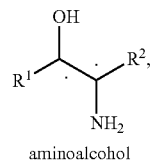

aminoalcohol wherein $R^1$ and $R^2$ are independently selected optionally substituted $C_1$-$C_{10}$-alkyl, cycloalkyl, or aryl. As opposed to a one-step process that uses the same reaction conditions for both reactions, Japanese Patent 2915161 discusses use of different reaction conditions for each reaction. Japanese Patent 2915161 characterizes the first step as a hydrogenation that may be carried out with $H_2$ in the presence of a monovalent rhodium complex and a ligand. The ligand corresponds in structure to the following formula:

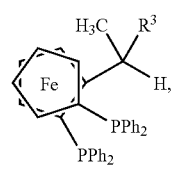

wherein Fe is ferrocene, and $R^3$ is hydroxy or an amine substituted with alkyl or cycloalkyl. Japanese Patent 2915161 characterizes the second step as a reduction that may be carried out using a metal hydride or using hydrogenation with $H_2$ in the presence of a Raney nickel or rhodium catalyst. Japanese Patent 2915161 does not discuss double-hydrogenations of any ketooxime to selectively form a stereoisomer of 6-amino-7-hydroxy-4,5,6,7-tetrahydro-imidazo[4,5,1-jk][1]-benzazepin-2[1H]-one or a salt thereof.

Japanese Patent Ref 2001-106664 discusses two-step hydrogenations of ketooximes. In the first step, the keto group is reduced using hydrogen with a homogeneous catalyst that comprises a metal complex of a ligand with a metal from transition group VIII. In the second step, the oxime group is reduced with borane. This reference does not discuss double-hydrogenations of any ketooxime to selectively form a stereoisomer of 6-amino-7-hydroxy-4,5,6,7-tetrahydro-imidazo[4,5,1-jk][1]-benzazepin-2[1H]-one or a salt thereof.

Thus, there still exists a need for processes (particularly commercially-viable processes) that may be used to selectively make a stereoisomer of 6-amino-7-hydroxy-4,5,6,7-tetrahydro-imidazo[4,5,1-jk][1]-benzazepin-2[1H]-one, and, in turn, a stereoisomer of zilpaterol, particularly a trans stereoisomer. This invention provides such a process.

SUMMARY OF THE INVENTION

Briefly, therefore, this invention is directed, in part, to a process for selectively synthesizing a stereoisomer of 6-amino-7-hydroxy-4,5,6,7-tetrahydro-imidazo[4,5,1-jk][1]-benzazepin-2[1H]-one or a salt thereof (also known as "7-amino-6-hydroxy-6,7,8,9-tetrahydro-2H-2,9a-diazabenzo[cd]azulene-1-one"). This process comprises reacting 4,5-dihydro-imidazo[4,5,1-jk][1]benzazepin-2,6,7[1H]-trione-6-oxime (also known as "imidazo[4,5,1-jk][1]benzazepine-2,6,7(1H)-trione, 4,5-dihydro-, 6-oxime" or "8,9-dihydro-2H-2,9a-diazabenzo[cd]azulene-1,6,7-trione-7-oxime") or a salt thereof with $H_2$ in the presence of a catalyst. The catalyst comprises a metal complex of a ligand with a metal from transition group VIII.

This invention also is directed, in part, to a process for selectively synthesizing a stereoisomer of zilpaterol or a salt thereof. This process comprises reacting 4,5-dihydro-imidazo[4,5,1-jk][1]benzazepin-2,6,7[1H]-trione-6-oxime with H₂ in the presence of a catalyst to selectively form a stereoisomer of 6-amino-7-hydroxy-4,5,6,7-tetrahydro-imidazo[4,5,1-jk][1]-benzazepin-2[1H]-one or a salt thereof, which, in turn, is converted to zilpaterol or a salt thereof. The catalyst used in the reaction forming the 6-amino-7-hydroxy-4,5,6,7-tetrahydro-imidazo[4,5,1-jk][1]-benzazepin-2[1H]-one (or a salt thereof) comprises a metal complex of a ligand with a metal from transition group VIII.

This invention also is directed, in part, to a method of feeding an animal. This method comprises feeding to an animal (e.g., a bovine animal, a swine animal, a sheep, or a bird) a zilpaterol stereoisomer selectively made by a process of this invention. Such feeding methods may be used, for example, to increase the animal's rate of weight gain, improve the animal's feed efficiency, and/or increase the animal's carcass leanness.

This invention also is directed, in part, to use for a zilpaterol stereoisomer selectively made by a process of this invention to make a medicament. Potential uses for such a medicament include increasing an animal's rate of weight gain, improving an animal's feed efficiency, and/or increasing an animal's carcass leanness.

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

This invention is directed, in part, to a process for selectively synthesizing a stereoisomer of 6-amino-7-hydroxy-4,5,6,7-tetrahydro-imidazo[4,5,1-jk][1]-benzazepin-2[1H]-one from 4,5-dihydro-imidazo[4,5,1-jk][1]benzazepin-2,6,7[1H]-trione-6-oxime:

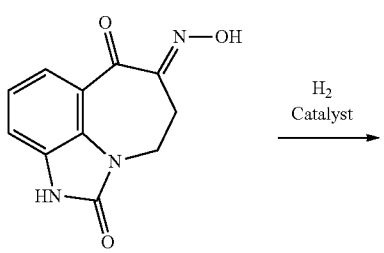
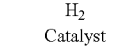

4,5-dihydro-imidazol[4,5,1-jk][1]
benzazepin-2,6,7[1H]-trione-6-oxime

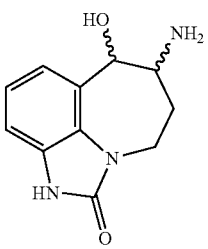

6-amino-7-hydroxy-4,5,6,7-tetrahydro-
imidazol[4,5,1-jk][1]-benzazepin-2[1H]-one This is a double-hydrogenation reaction. Each wavy line in the product structure represents that the corresponding substituent may have either an R or S configuration. In other words, this process may be used to selectively make one of the four possible stereoisomers:

Formula (IIa)

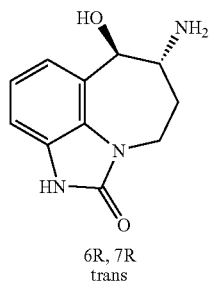

6R, 7R
trans

Formula (IIb)

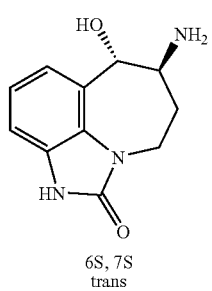

6S, 7S
trans

Formula (IIc)

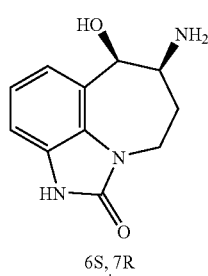

6S, 7R
cis

Formula (IId)

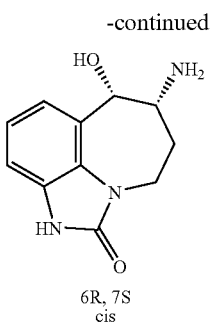

6R, 7S
cis

The term "selective," as used in this context, means that the amount of one stereoisomer made by the process constitutes greater than 50% (and more typically greater than about 60%, greater than about 75%, or greater than about 85%) of the total amount of all the 6-amino-7-hydroxy-4,5,6,7-tetrahydro-imidazo[4,5,1-jk][1]-benzazepin-2[1H]-one stereoisomers made. It has been discovered that the process of this invention is particularly suitable for selectively synthesizing a trans isomer of 6-amino-7-hydroxy-4,5,6,7-tetrahydro-imidazo[4,5,1-jk][1]-benzazepin-2[1H]-one. In some embodiments, the process is used to selectively make the 6R,7R trans isomer (Formula (IIa)).

It has been discovered in accordance with this invention that this double-hydrogenation reaction can be advantageously performed in a one-pot and single-step process. Specifically, when 4,5-dihydro-imidazo[4,5,1-jk][1]benzazepin-2,6,7[1H]-trione-6-oxime is reacted to form 6-amino-7-hydroxy-4,5,6,7-tetrahydro-imidazo[4,5,1-jk][1]-benzazepin-2[1H]-one, two hydrogenation reactions occur: the hydrogenation of a ketone to form a hydroxy, and the hydrogenation of an oxime to form an amine. Both these reactions occur using the reaction conditions of this invention employing the same catalyst. Thus, it is unnecessary to isolate any intermediate and/or subject the reaction mixture to separate hydrogenation conditions to initiate or complete the second of the two hydrogenation reactions. This translates into, for example, potential savings with respect to manpower, equipment costs, solvent use, and loss of any reagent or product that may occur during any isolation step; or avoidance of any potential epimerization of the first-generated stereocenter while generating the second.

The 4,5-dihydro-imidazo[4,5,1-jk][1]benzazepin-2,6,7[1H]-trione-6-oxime reagent may be prepared from commercially available ingredients using, for example, methods known in the art. As indicated above in the Background of the Invention section, such methods include those described in U.S. Pat. No. 4,585,770 (the full text of U.S. Pat. No. 4,585,770 is incorporated by reference into this patent).

The catalyst used in the process of this invention comprises a metal complex of a chiral ligand and a metal from transition group VIII of the Periodic Table of the Elements. Although the metal complex is normally made from a single ligand and a single metal from transition group VIII, the metal complex may comprise additional ligands and/or metals.

In general, the catalyst comprises a homogeneous catalyst, i.e., essentially all (or all) the catalyst is dissolved. In some embodiments, at least about 50% (and, more preferably, at least about 75%, at least about 90%, at least about 95%, at least about 99%, at least about 99.9%, or about 100%) by weight of the catalyst is dissolved in the solvent.

In some embodiments, the ligand comprises one or more ligands corresponding in structure to Formula (A) or Formula (B):

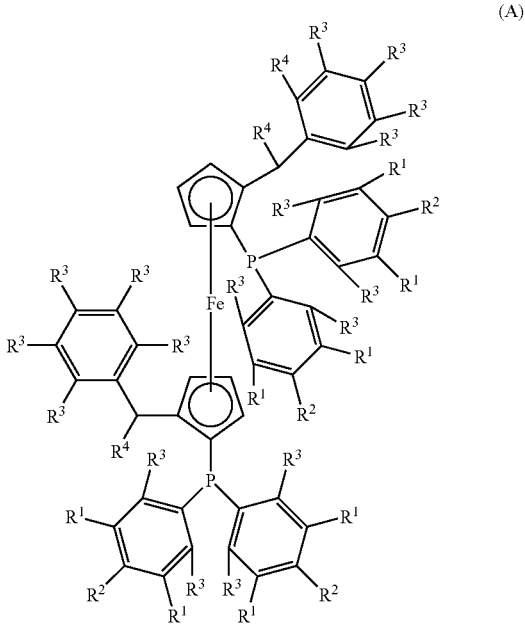

(A)

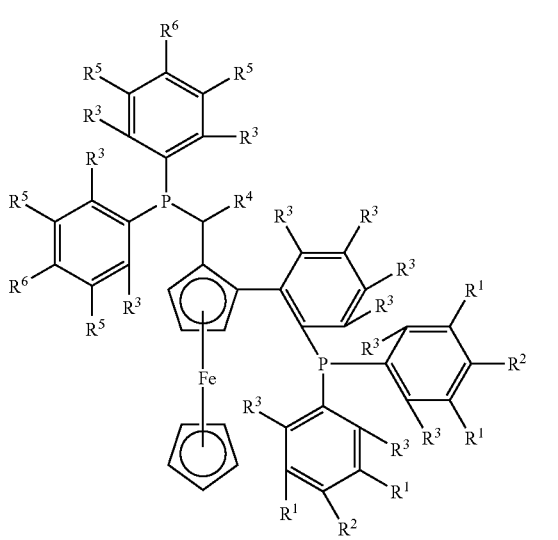

(B)

Here,

Each of $R^1$, $R^2$, $R^5$, and $R^6$ is independently hydrogen, $C_1$-$C_6$-alkyl, hydroxy, or $C_1$-$C_6$-alkoxy. Any such $C_1$-$C_6$-alkyl or $C_1$-$C_6$-alkoxy is, in turn, optionally substituted by one or more halogen.

Each $R^3$ is independently hydrogen or $C_1$-$C_6$-alkyl.

Each $R^4$ is independently hydrogen, $C_1$-$C_6$-alkyl, or $NR^7R^8$.

Each of $R^7$ and $R^8$ is independently hydrogen or $C_1$-$C_6$-alkyl. Alternatively, $R^7$ and $R^8$, together with the nitrogen to which they are commonly attached, form a saturated heterocycle.

The term "independently" is used to characterize each substituent as being selected independent of the other substituents. Thus, for example, each $R^1$ is selected independent of the other $R^1$, $R^2$, $R^5$, and $R^6$ substituents, and, therefore, may be the same as or different than each of the other $R^1$ substituents, as well as the same as or different than each of the $R^2$, $R^5$, and $R^6$ substituents.

In instances wherein both $R^4$'s in Formula (A) are $NR^7R^8$, each $NR^7R^8$ substituent is independently selected. Thus, for example, it is possible that in one of the $R^4$ substituents, the $R^7$ and $R^8$ are independently hydrogen or $C_1$-$C_6$-alkyl, while in the other $R^4$ substituent, $R^7$ and $R^8$ (together with the nitrogen to which they are commonly attached) form a saturated heterocycle.

In some embodiments, each $R^3$ is identical to the other $R^3$ substituents. In some such embodiments, for example, each $R^3$ is hydrogen. Here, the ligand corresponds in structure to Formula (AA) or Formula (BB):

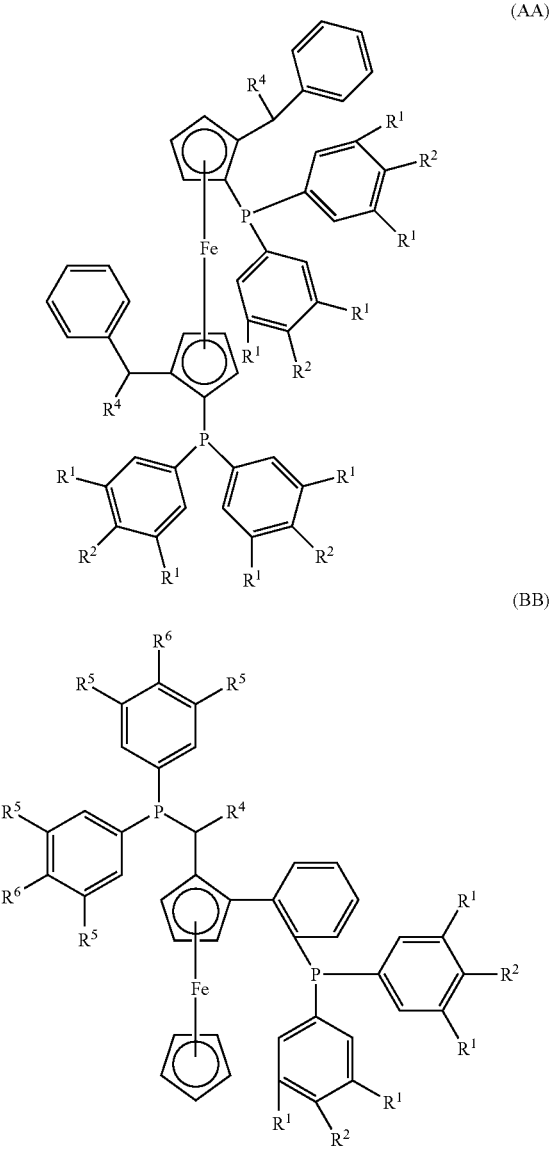

(AA)

(BB)

In some embodiments, each $R^1$ is independently hydrogen or $C_1$-$C_6$-alkyl optionally substituted by one or more halogen. In some such embodiments, for example, each $R^1$ is independently hydrogen or methyl optionally substituted by one or more halogen. In some such embodiments, each $R^1$ is independently hydrogen, $CH_3$, or $CF_3$. In some embodiments, each $R^1$ is identical to the other $R^1$ substituents. In some such embodiments, for example, each $R^1$ is H. In other embodiments, each $R^1$ is $CH_3$. And, in still other embodiments, each $R^1$ is $CF_3$.

In some embodiments, each $R^2$ is independently hydrogen or $C_1$-$C_6$-alkoxy. In some embodiments, each $R^2$ is independently hydrogen or methoxy. In some embodiments, each $R^2$ is identical to the other $R^2$ substituent(s). In some such embodiments, for example, each $R^2$ is hydrogen. And, in other embodiments, for example, each $R^2$ is methoxy.

In some embodiments, each $R^4$ is independently $C_1$-$C_6$-alkyl or $NR^7R^8$. In some such embodiments, for example, an $R^4$ is methyl. In other embodiments, an $R^4$ is independently selected $NR^7R^8$. In some embodiments wherein the ligand corresponds to Formula (A), each $R^4$ is identical to the other $R^4$ substituent. In some such embodiments, for example, each $R^4$ is $NR^7R^8$.

In some embodiments, each $R^5$ is independently $C_1$-$C_6$-alkyl substituted by one or more halogen. In some embodiments, each $R^5$ is identical to the other $R^5$ substituents. In some such embodiments, for example, each $R^5$ is independently methyl substituted by one or more halogen. In other embodiments, each $R^5$ is $CF_3$.

In some embodiments, each $R^6$ is identical to the other $R^6$ substituent. In some such embodiments, for example, each $R^6$ is hydrogen.

In some embodiments, each of $R^7$ and $R^8$ is independently $C_1$-$C_6$-alkyl. In some embodiments, for example, each of $R^7$ and $R^8$ is methyl. In some such embodiments wherein the ligand corresponds to Formula (A), each $R^4$ is dimethylamino ($N(CH_3)_2$).

In some embodiments, $R^7$ and $R^8$, together with the nitrogen to which they are commonly attached, form a saturated heterocycle. The saturated heterocycle preferably has a total of 5 to 6 ring atoms. At least one ring atom is nitrogen (i.e., the nitrogen to which $R^7$ and $R^8$ are commonly attached). The remaining ring atoms are independently selected from the group consisting of carbon, oxygen, nitrogen, and sulfur. Examples of such heterocycles include pyrrolidinyl, piperidinyl, and morpholinyl.

In some embodiments wherein the ligand corresponds to Formula (A), each $R^4$ is a saturated heterocycle.

In some embodiments, $R^7$ and $R^8$, together with the nitrogen to which they are commonly attached, form a pyrrolidinyl. In some such embodiments wherein the ligand corresponds to Formula (A), each $R^4$ is a pyrrolidinyl.

In some embodiments, the ligand corresponds to Formula (A). In some such embodiments, for example, each $R^1$ is H. In other embodiments, each $R^1$ is $CH_3$. In other embodiments, each $R^1$ is $CF_3$. In other embodiments, each $R^2$ is H. In other embodiments, each $R^2$ is $OCH_3$. In other embodiments, each $R^3$ is H. In other embodiments, each $R^4$ is $N(CH_3)_2$. And, in other embodiments, each $R^4$ is pyrrolidinyl.

Examples of ligands corresponding in structure to Formula (A) include, for example, the ligand corresponding in structure to Formula (A-1) (i.e., a ligand wherein each $R^1$ is $CH_3$, each $R^2$ is $OCH_3$, each $R^3$ is H, and each $R^4$ is $N(CH_3)_2$):

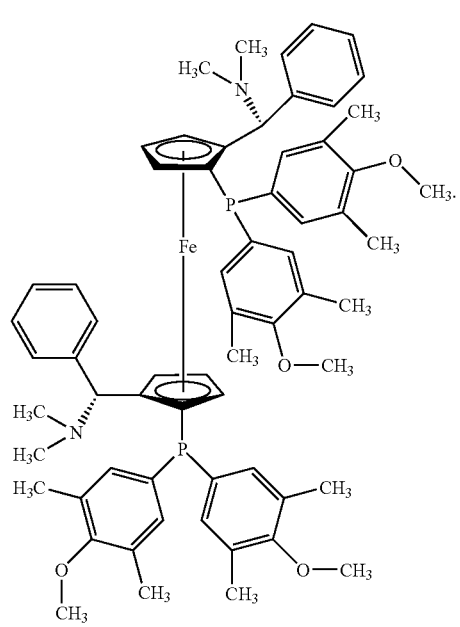

(A-1)

This and other such ligands are discussed in, for example, US Patent Appl. Publ. 2006/0241315 (incorporated by reference into this patent).

Examples of ligands encompassed by Formula A also include, for example, the enantiomer of Formula (A-1). That enantiomer corresponds to Formula (A-1B):

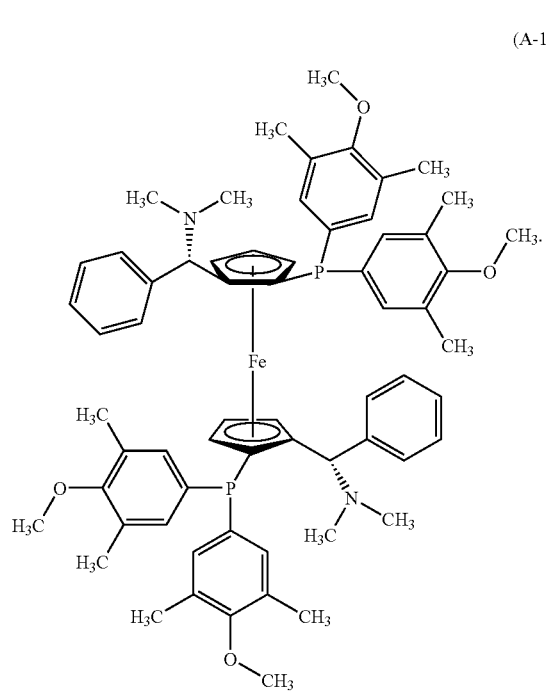

(A-1B)

Examples of ligands encompassed by Formula (A) also include, for example, the ligand corresponding in structure to Formula (A-2) (i.e., a ligand wherein each $R^1$ is H, each $R^2$ is H, each $R^3$ is H, and each $R^4$ is $N(CH_3)_2$) or the enantiomer thereof:

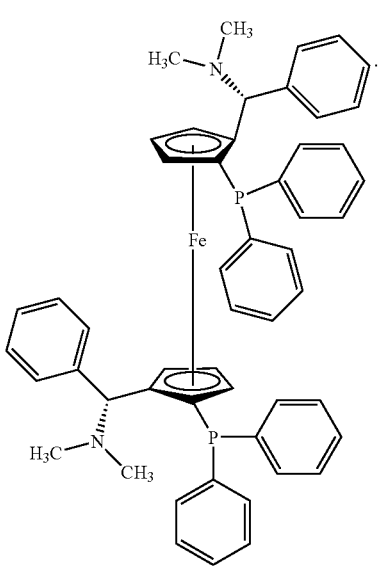

(A-2)

The ligand of Formula (A-2) and other such ligands are discussed in, for example, U.S. Pat. No. 6,348,620 (incorporated by reference into this patent).

Examples of ligands encompassed by Formula A also include, for example, the ligand corresponding in structure to Formula (A-3) (i.e., a ligand wherein each $R^1$ is $CF_3$, each $R^2$ is H, each $R^3$ is H, and each $R^4$ is $N(CH_3)_2$) or the enantiomer thereof:

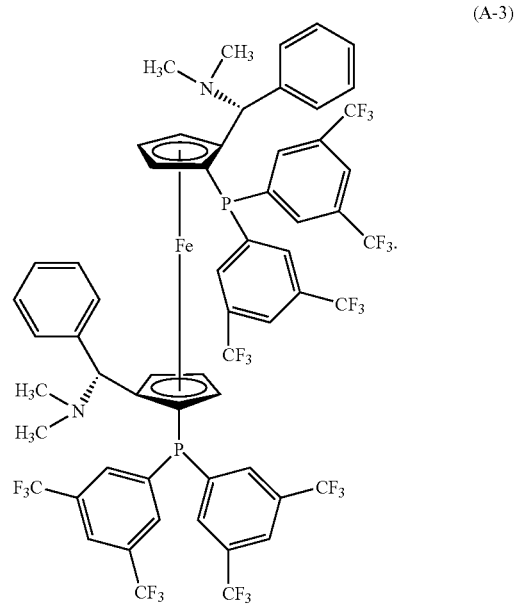

(A-3)

Examples of ligands encompassed by Formula A also include, for example, the ligand corresponding in structure to Formula (A-4) (i.e., a ligand wherein each $R^1$ is H, each $R^2$ is H, each $R^3$ is H, and each $R^4$ is pyrrolidinyl) or the enantiomer thereof:

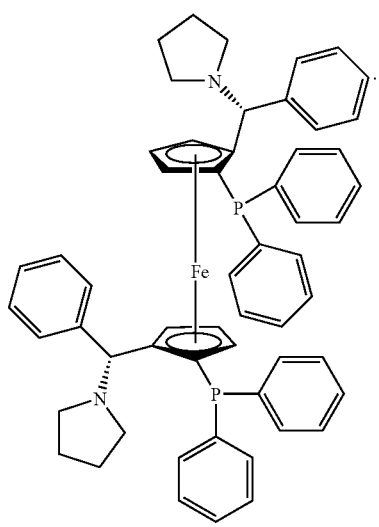
(A-4)

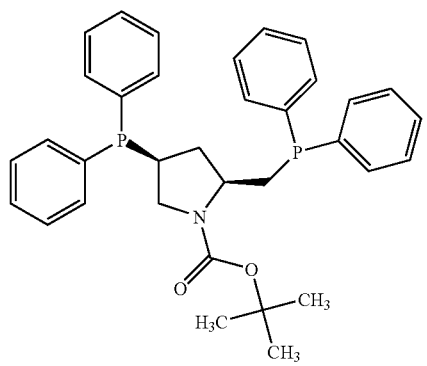
C-1

In some embodiments, the ligand corresponds to Formula (B). In some such embodiments, for example, each $R^1$ is $CH_3$. In other embodiments, each $R^2$ is $OCH_3$. In other embodiments, each $R^3$ is H. In other embodiments, each $R^4$ is $CH_3$. In other embodiments, each $R^5$ is independently methyl substituted by one or more halogen. In other embodiments, each $R^5$ is $CF_3$. And, in other embodiments, each $R^6$ is H.

Examples of ligands encompassed by Formula (B) include, for example, the ligand corresponding in structure to Formula (B-1) (i.e., a ligand wherein $R^1$ is $CH_3$, each $R^2$ is $OCH_3$, each $R^3$ is H, $R^4$ is $CH_3$, each $R^5$ is $CF_3$, and each $R^6$ is H) or the enantiomer thereof:

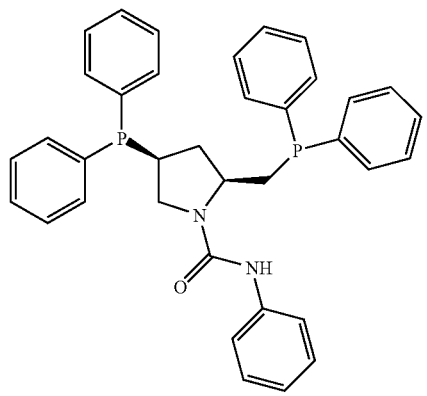
C-2

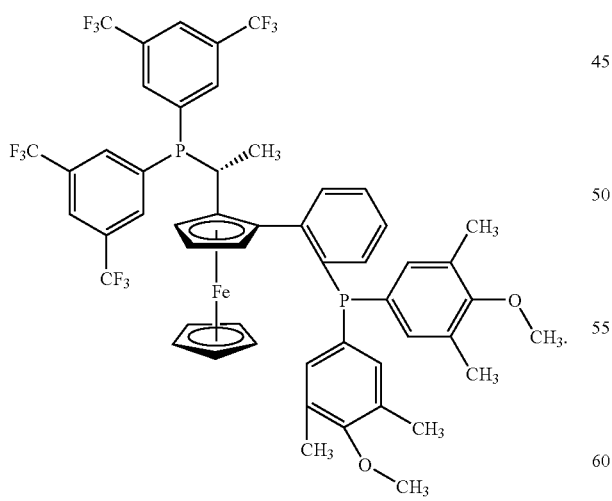
(B-1)

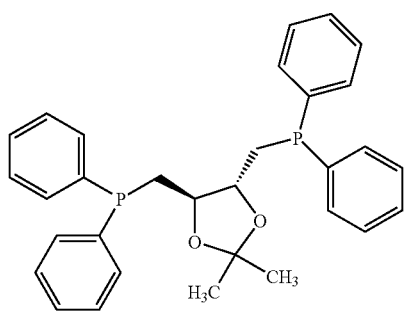
C-3

A wide range of other ligands also are generally suitable for this reaction. Such ligands include, for example, ligands (and enantiomers thereof) corresponding in structure to the following:

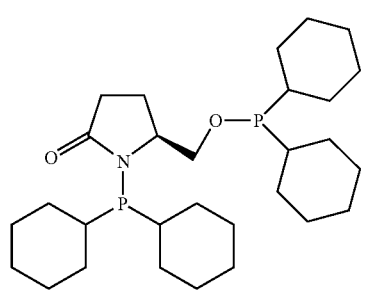
C-4

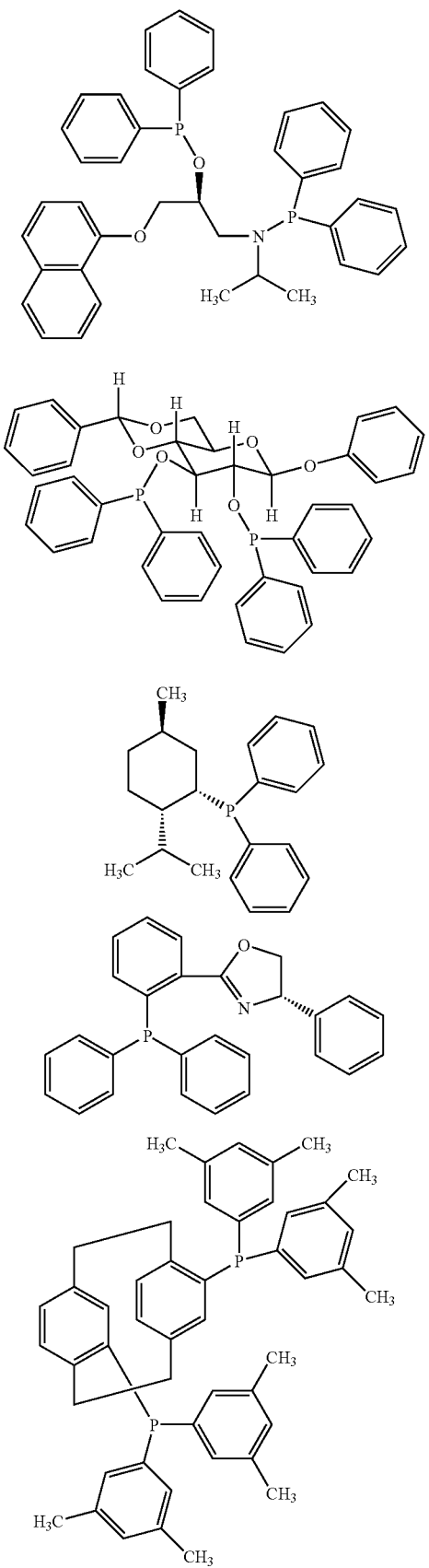
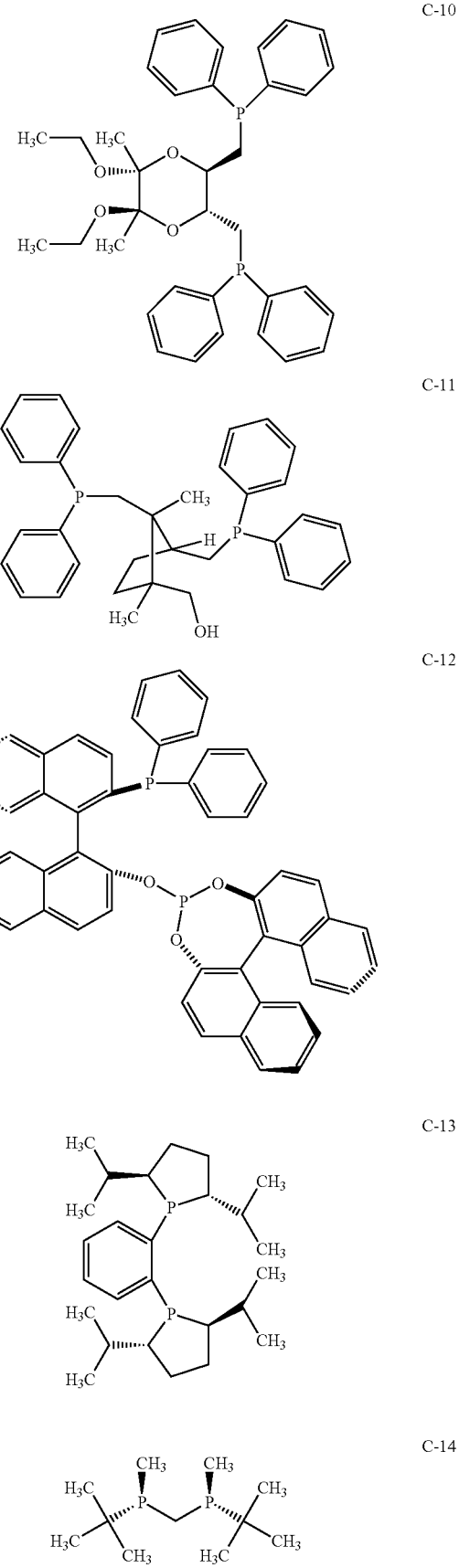

-continued
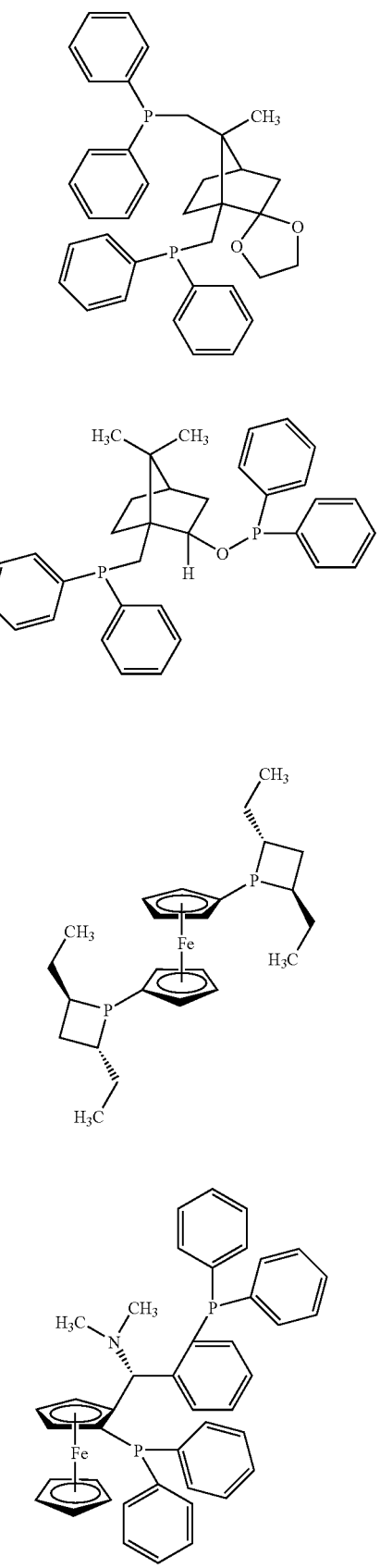
C-15
C-16
C-17
C-18
-continued
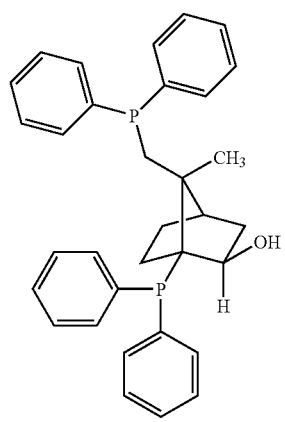
C-19
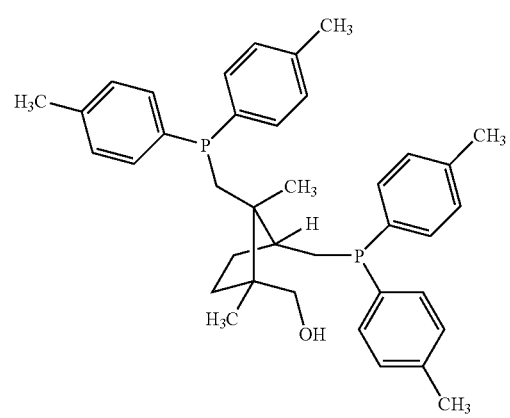
C-20
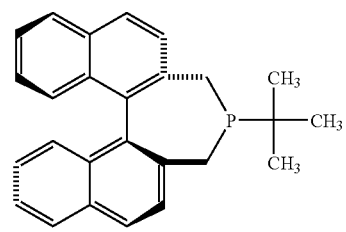
C-21
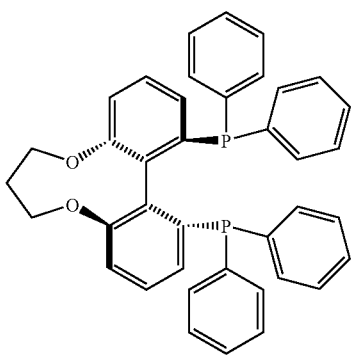
C-22

C-23
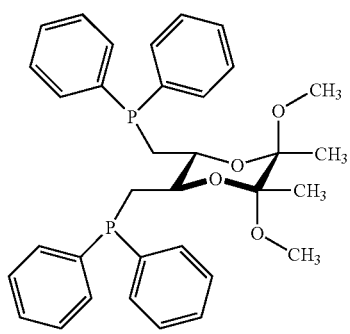
C-24
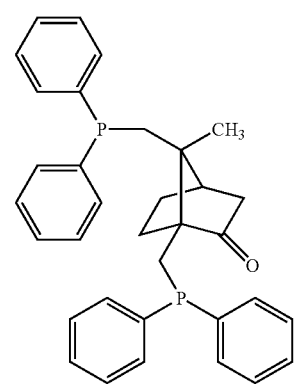
C-25
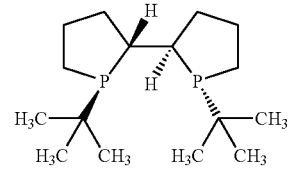
C-26
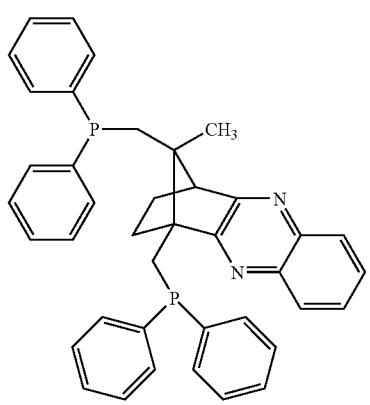
C-27
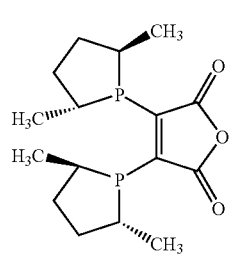
C-28
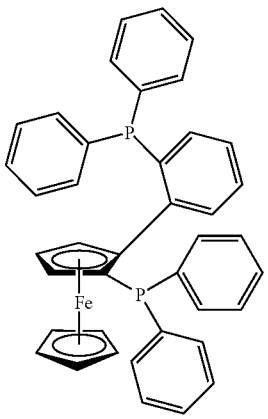
C-29
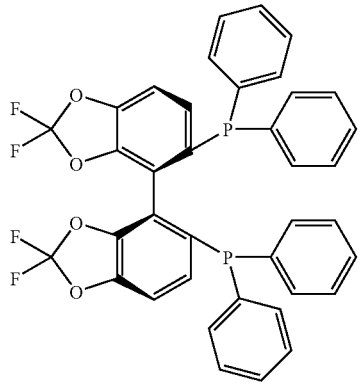
C-30
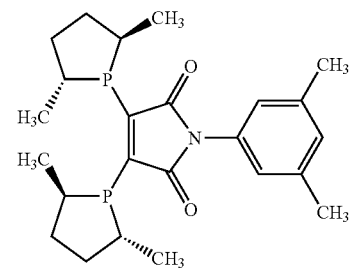
C-31
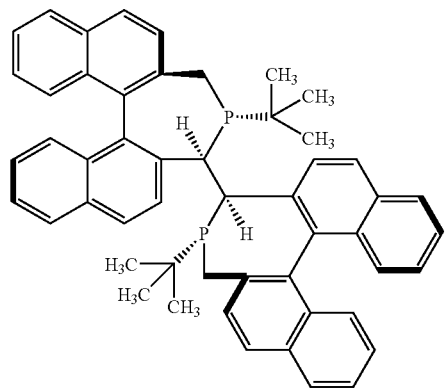
The selectivity of the reaction toward a particular stereoisomer product can generally be changed toward its enantiomer product by using the other enantiomeric form of the catalyst ligand.
Metals from transition group VIII include iron ("Fe"), cobalt ("Co"), nickel ("Ni"), rhodium ("Rh"), ruthenium ("Ru"), iridium ("Ir"), osmium ("Os"), platinum ("Pt"), and palladium ("Pd"). In some embodiments, the transition group VIII metal comprises one or more of rhodium, ruthenium, and iridium.

In some embodiments, the metal complex comprises ruthenium.

In some embodiments wherein the metal complex comprises ruthenium, the metal complex comprises $RuCl_2Ligand(DMF)_x$, wherein x is a number greater than zero. The acronym "DMF" corresponds to dimethylformamide, which also is known as "N,N-dimethylformamide." This complex can generally be prepared by, for example, mixing $[Ru(C_6H_6)Cl_2]_2$ with the ligand in DMF at 100° C. for 10 min.

In other embodiments wherein the metal complex comprises ruthenium, the metal complex comprises [Ru(ligand)(p-cymene)Cl]Cl. This complex can be prepared by, for example, mixing $[Ru(p\text{-}cymene)Cl_2]_2$ with the ligand in ethanol or an ethanol/dichloromethane solvent mixture at 50° C. for 2 hours.

In other embodiments wherein the metal complex comprises ruthenium, the metal complex comprises Ru(ligand)$Br_2$. This complex can be prepared by, for example, mixing $Rh(1,5\text{-}cyclo\text{-}octadiene)(2\text{-}methylallyl)_2$, the ligand, and HBr in acetone.

In other embodiments wherein the metal complex comprises ruthenium, the metal complex comprises Ru(ligand)(acetylacetonate)$_2$ (or "Ru(ligand)(acac)$_2$"). This complex can be prepared by, for example, mixing $[Ru(\eta^4\text{-}2,4\text{-}C_6H_{10})(acetylacetonate)_2]$ and the ligand in tetrahydrofuran ("THF").

In some embodiments where the metal complex comprises ruthenium, the ligand comprises one or more ligands selected from the group consisting of Formula (C-1), Formula (C-2), Formula (C-6), Formula (C-7), Formula (C-8), Formula (C-9), Formula (C-11), Formula (C-12), Formula (C-13), Formula (C-14), Formula (C-16), Formula (C-17), Formula (C-21), Formula (C-22), Formula (C-25), Formula (C-28), Formula (C-29), Formula (C-30), Formula (C-31), and the enantiomers thereof.

In some embodiments, the metal complex comprises rhodium.

In some embodiments wherein the metal complex comprises rhodium, the metal complex may be prepared from [Rh—Z-diene]dimer. Here, Z is halogen. Examples of such rhodium compounds include, for example, $[RhCl(1,5\text{-}cyclo\text{-}octadiene)]_2$, $[RhCl(1,5\text{-}hexaadiene)]_2$, and $[RhCl(1,5\text{-}norbornadiene)]_2$.

Alternatively, the metal complex comprising rhodium may be prepared from, for example, $[Rh\text{-}(diene)_2]^+Y$. Here, Y is $[BF_4^-]$, $[ClO_4^-]$, $[PF_6^-]$, or another anion that has no ligand capacity. Examples of such rhodium compounds include, for example, $[Rh(norbornadiene)_2]^+ClO_4^-$, $[Rh(1,5\text{-}cyclo\text{-}octadiene)_2]^+ClO_4^-$, $[Rh(1,5\text{-}cyclo\text{-}octadiene)_2]^+BF_4^-$ (also known as "Rh(COD)$_2$BF$_4$"), $[Rh(1,5\text{-}cyclo\text{-}octadiene)_2]^+PF_6^-$, $[Rh(1,5\text{-}hexadiene)_2]^+ClO_4^-$, $[Rh(1,5\text{-}hexadiene)_2]^+BF_4^-$, $[Rh(1,5\text{-}hexadiene)_2]^+PF_6^+$, $[Rh(norbornadiene)_2]^+BF_4^-$, and $[Rh(norbornadiene)_2]^+PF_6^-$.

The metal complex catalyst may be prepared from the above rhodium compounds by, for example, mixing the ligand with the rhodium compound at a molar ratio of ligand-to-rhodium of about 1:1. In some such embodiments, a slight excess of ligand is used. In some embodiments, the ligand and rhodium compound are mixed in the presence of a solvent (e.g., a solvent used in the hydrogenation reaction or dichloromethane) before being added to the reaction mixture. In other embodiments, the ligand and rhodium compound are mixed by being separately added to the hydrogenation reaction mixture. In these embodiments, the ligand/rhodium mixture preferably is used within about 3 hours of its preparation.

In some embodiments, the catalyst comprises Rh(1,5-cyclo-octadiene)ligandBF$_4$ (or "Rh(COD)ligandBF$_4$").

In some embodiments where the metal complex comprises rhodium, the ligand comprises one or more ligands (or stereoisomers thereof) selected from the group consisting of ligands corresponding to Formula (A) and Formula (B). In some such embodiments, for example, the ligand comprises one or more ligands selected from the group consisting of ligands corresponding to Formula (AA) and Formula (BB). In other such embodiments, the ligand may, for example, comprise one or more ligands selected from the group consisting of ligands corresponding to Formula (A-1), Formula A-2), Formula (A-4), Formula (B-1), and the enantiomers thereof.

In some embodiments where the metal complex comprises rhodium, the ligand comprises one or more ligands selected from the group consisting of ligands corresponding to Formula (C-1), Formula (C-2), Formula (C-3), Formula (C-4), Formula (C-5), Formula (C-10), Formula (C-15), Formula (C-18), Formula (C-19), Formula (C-20), Formula (C-23), Formula (C-24), Formula (C-26), Formula (C-27), Formula (C-31), and the enantiomers thereof.

The molar ratio of 4,5-dihydro-imidazo[4,5,1-jk][1]benzazepin-2,6,7[1H]-trione-6-oxime to the catalyst charged to the hydrogenation reactor may vary. The ratio preferably is no less than about 10:1. In some embodiments, for example, the ratio is at least about 25:1, at least about 50:1, at least about 100:1, or at least about 200:1. In some embodiments, the ratio is from about 50:1 to about 500:1, from about 50:1 to about 400:1, or from about 50:1 to about 200:1. In some such embodiments, for example, the ratio is from about 50:1 to about 150:1, from about 50:1 to about 100:1, or about 50:1. In other embodiments, the ratio is from about 100:1 to about 200:1, or from about 100:1 to about 150:1.

The hydrogenation of 4,5-dihydro-imidazo[4,5,1-jk][1]benzazepin-2,6,7[1H]-trione-6-oxime (or its salt) is generally conducted in a solvent. Various solvents may be used. The solvent preferably is non-reactive with the reagents, products, and any other ingredients in the reaction mixture. Examples of such solvents generally include, for example, methanol, water, tetrahydrofuran, isopropyl alcohol, toluene, ethyl acetate, and dimethylformamide. In some embodiments, the solvent comprises methanol, water, tetrahydrofuran, or isopropyl alcohol. In some such embodiments, for example, the solvent comprises methanol. In other embodiments, the solvent comprises isopropyl alcohol. Other solvents are contemplated, such as, for example, formamides (e.g., N-methylpyrrolidinone), aliphatic alcohols (e.g., ethanol), chlorinated hydrocarbons (e.g., chloroform), ethers (e.g., dioxane), aromatic hydrocarbons (e.g., benzene), and esters (e.g., methyl acetate).

Mixtures of solvents also may be used. Such mixtures may, for example, comprise two or more of methanol, water, tetrahydrofuran, isopropyl alcohol, toluene, ethyl acetate, dimethylformamide, and dichloromethane ("DCM"). In some embodiments, the solvent comprises two or more of methanol, water, tetrahydrofuran, or isopropyl alcohol. In some such embodiments, for example, the solvent comprises methanol and water, methanol and tetrahydrofuran, isopropyl alcohol and tetrahydrofuran, or toluene and tetrahydrofuran. In other embodiments, for example, the solvent comprises methanol and water. The volume ratio may vary in solvent mixtures. To illustrate, in some embodiments when the solvent comprises methanol and tetrahydrofuran, the volume ratio of methanol to tetrahydrofuran may be, for example, about 1:1. In some embodiments when the solvent comprises toluene and tetrahydrofuran, the volume ratio of toluene to tetrahydrofuran may be, for example, about 1:1. In some embodiments when the solvent comprises methanol and water, the volume ratio of methanol to water may be, for example, about 10:1. In some embodiments wherein the solvent comprises methanol and DCM, the volume ratio of methanol to DCM is about 24:1.

Typically, the amount of solvent is sufficient to, for example, prevent (or essentially prevent) the reagents, products, and other ingredients in the reaction mixture from sticking to the reactor, and promote homogenous distribution of the reagents. To illustrate, in some embodiments, the ratio of solvent to 4,5-dihydro-imidazo[4,5,1-jk][1]benzazepin-2,6,7[1H]-trione-6-oxime may be, for example, from about 34 to about 35 ml/g. In other embodiments (e.g., laboratory scale embodiments), the ratio of solvent to 4,5-dihydro-imidazo[4,5,1-jk][1]benzazepin-2,6,7[1H]-trione-6-oxime may be, for example, from about 43 to about 44 ml/g. And in some embodiments, the ratio of solvent (e.g., methanol/DCM at a volume ratio of 24:1) to 4,5-dihydro-imidazo[4,5,1-jk][1]benzazepin-2,6,7[1H]-trione-6-oxime may be, for example, from about 22 to about 23 ml/g.

In some embodiments, the hydrogenation of 4,5-dihydro-imidazo[4,5,1-jk][1]benzazepin-2,6,7[1H]-trione-6-oxime (or its salt) may be conducted in the presence of a base. In some embodiments, the base comprises one or more inorganic bases, such as, for example, potassium hydroxide ("KOH"). In other embodiments, the base comprises one or more organic bases, such as, for example, triethylamine. In still other embodiments, the base comprises both inorganic and organic bases. The amount of base may vary. In some embodiments for example, the concentration of base in the reaction mixture at the beginning of the hydrogenation is no greater than about 3 eq. (or from about 1 to about 2 eq.) relative to the amount of 4,5-dihydro-imidazo[4,5,1-jk][1]benzazepin-2,6,7[1H]-trione-6-oxime (or its salt).

In some embodiments wherein the hydrogenation is conducted in the presence of a base, the catalyst comprises ruthenium. In other embodiments wherein the hydrogenation is conducted in the presence of a base, the catalyst comprises rhodium.

In some embodiments wherein the hydrogenation is conducted in the presence of an base (e.g., KOH), the catalyst ligand comprises a ligand selected from the group of ligands selected from the group consisting of Formula (C-1), Formula (C-2), Formula (C-3), Formula (C-6), Formula (C-7), Formula (C-8), Formula (C-9), Formula (C-11), Formula (C-12), Formula (C-13), Formula (C-14), Formula (C-16), Formula (C-17), Formula (C-21), Formula (C-25), Formula (C-28), Formula (C-30), and the enantiomers thereof.

In some embodiments, the hydrogenation of 4,5-dihydro-imidazo[4,5,1-jk][1]benzazepin-2,6,7[1H]-trione-6-oxime (or its salt) may be conducted in the presence of an acid. The presence of an acid may, for example, stabilize the reaction, accelerate the reaction, and/or increase conversion. In some embodiments, for example, the acid comprises one or more strong inorganic acids, such as, for example, a mineral acid, such as sulfuric acid ("$H_2SO_4$"). In other embodiments, the acid comprises one or more strong organic acids, such as, for example, trifluoroacetic acid ("$CF_3CO_2H$"). In still other embodiments, the acid comprises both inorganic and organic acids. The amount of acid may vary. In some embodiments for example, the concentration of acid in the reaction mixture at the beginning of the hydrogenation is no greater than about 3 eq. (or from about 1 to about 2 eq.) relative to the amount of 4,5-dihydro-imidazo[4,5,1-jk][1]benzazepin-2,6,7[1H]-trione-6-oxime (or its salt).

In some embodiments wherein the hydrogenation is conducted in the presence of a acid, the catalyst comprises ruthenium. In other embodiments wherein the hydrogenation is conducted in the presence of a acid, the catalyst comprises rhodium.

In some embodiments wherein the hydrogenation is conducted in the presence of an acid (e.g., $CF_3CO_2H$), the catalyst ligand corresponds in structure to Formula (A-2) or the enantiomer thereof. In other embodiments wherein the hydrogenation is conducted in the presence of an acid, the catalyst ligand comprises a ligand selected from the group of ligands selected from the group consisting of Formula (A-1), Formula (A-4), Formula (B-1), Formula (C-3), Formula (C-5), Formula (C-19), Formula (C-24), Formula (C-26), and the enantiomers thereof.

The hydrogenation of 4,5-dihydro-imidazo[4,5,1-jk][1]benzazepin-2,6,7[1H]-trione-6-oxime (or its salt) may be conducted over a wide range of temperatures. Typically, the reaction is conducted at a temperature that is not greater than the boiling point of the solvent, and more typically is less than the boiling point. In general, the temperature preferably is no greater than about 90° C. The temperature also preferably is at least about 20° C. during at least a portion (and, more preferably, essentially all, or all) of the reaction. In some embodiments, for example, the temperature is from about 20 to about 80° C., or from about 25 to about 80° C. In some such embodiments, the temperature is no greater than about 45° C., from about 25 to about 45° C., or from about 35 to about 45° C. For example, the temperature in some embodiments is from 35 to about 40° C., while the temperature in other embodiments is from about 40 to about 45° C. In other embodiments, the temperature is from about 50 to about 80° C., from about 50 to about 75° C., or from about 50 to about 65° C. Although lesser temperatures than the above ranges may generally be used, such temperatures tend to coincide with slower reaction rates. And, although greater temperatures may generally be used, such temperatures may coincide with greater production of undesirable byproducts.

The hydrogenation of 4,5-dihydro-imidazo[4,5,1-jk][1]benzazepin-2,6,7[1H]-trione-6-oxime (or a salt thereof) is generally conducted in the presence of $H_2$ or a source of $H_2$. In some embodiments, for example, the hydrogenation is conducted in the presence of $H_2$ or a mixture of $H_2$ and an inert gas. The hydrogenation may be conducted over a wide range of $H_2$ pressures. In general, the $H_2$ pressure is preferably at least about 1 bar, and generally greater than atmospheric pressure. The pressure also preferably is no greater than about 80 bars. In some embodiments (e.g., laboratory scale embodiments), for example, the pressure is from about 10 to about 70 bars, or from about 20 to about 70 bars. In some such embodiments, the pressure is from about 20 to about 60 bar. In other embodiments, the pressure is from about 40 to about 65 bars. For example, in some embodiments, the pressure is from about 40 to about 50 bar. In other embodiments, the pressure is from about 60 to about 65 bars. In some embodiments, the H₂ pressure is less than about 25 bar, less than about 16 bar, from about 2 to about 12 bar, from about 2 to about 7 bar, or from about 2 to about 5 bar.

The preferred reaction time (or residence time for a continuous reactor) will vary, and will depend on various factors, which may include, for example, the reaction temperature, catalyst type, catalyst concentration, H₂ pressure, 4,5-dihydro-imidazo[4,5,1-jk][1]benzazepin-2,6,7[1H]-trione-6-oxime concentration, molar ratio of 4,5-dihydro-imidazo[4,5,1-jk][1]benzazepin-2,6,7[1H]-trione-6-oxime to catalyst, characteristics of the solvent, presence of a base or acid, reactor configuration and size, rate of conversion acceptable to the user, etc. In a batch reactor, the reaction time is generally greater than about 1 minute, more typically greater than about 30 minutes, still more typically greater than about 2 hours, and still yet more typically greater than about 5 hours. The reaction time typically is no greater than about 36 hours, and more typically no greater than about 24 hours. In some embodiments, the reaction time is, for example, from about 18 to about 24 hours. Although reaction times less than these typical ranges may be used, such reaction times may coincide with lesser conversions. And, although greater reaction times may be used, such reaction times may coincide with greater production of impurities or inefficient use of equipment or manpower.

The reactor used for the double-hydrogenation may comprise various reactor types. In some embodiments, for example, the reactor is a stirred-tank reactor. Glass and glass-lined reactors are typically suitable, although any composition stable when exposed to the reaction mixture may be used.

Purification or isolation of the double-hydrogenation product may be achieved using, for example, various methods known in the art. This purified product may, in turn, be used to selectively make a stereoisomer of zilpaterol or a salt thereof. Alternatively, the double-hydrogenation product may, for example, be used to selectively make a stereoisomer of zilpaterol (or a salt thereof) without further purification or isolation.

In general, the 6-amino-7-hydroxy-4,5,6,7-tetrahydro-imidazo[4,5,1-jk][1]-benzazepin-2[1H]-one stereoisomer made in accordance with this invention is used to selectively make the corresponding zilpaterol stereoisomer. The term "selective," as used in the context of synthesizing a zilpaterol stereoisomer, means that the amount of one zilpaterol stereoisomer constitutes greater than 50% (and more typically greater than about 60%, greater than about 75%, or greater than about 85%) of the total amount of all the zilpaterol stereoisomers made. Given that the process is particularly suitable for selectively synthesizing a trans isomer of 6-amino-7-hydroxy-4,5,6,7-tetrahydro-imidazo[4,5,1-jk][1]-benzazepin-2[1H]-one, it follows that the process also is particularly suitable for selectively synthesizing the corresponding trans isomer of zilpaterol. In some embodiments, the process is used to selectively make the 6R,7R trans isomer of zilpaterol. Applicants have observed that the 6R,7R zilpaterol stereoisomer has a negative optical rotation, as measured by a polarimeter; thus, it also may be referred to as the "trans(−)" stereoisomer.

The 6-amino-7-hydroxy-4,5,6,7-tetrahydro-imidazo[4,5,1-jk][1]-benzazepin-2[1H]-one stereoisomer may be converted to the corresponding zilpaterol stereoisomer using various methods. In general, this may be achieved by, for example, reductive alkylation. For example, the 6-amino-7-hydroxy-4,5,6,7-tetrahydro-imidazo[4,5,1-jk][1]-benzazepin-2[1H]-one stereoisomer may be alkylated with acetone in the presence of a reducing agent to form the corresponding zilpaterol stereoisomer as illustrated in the following reaction scheme:

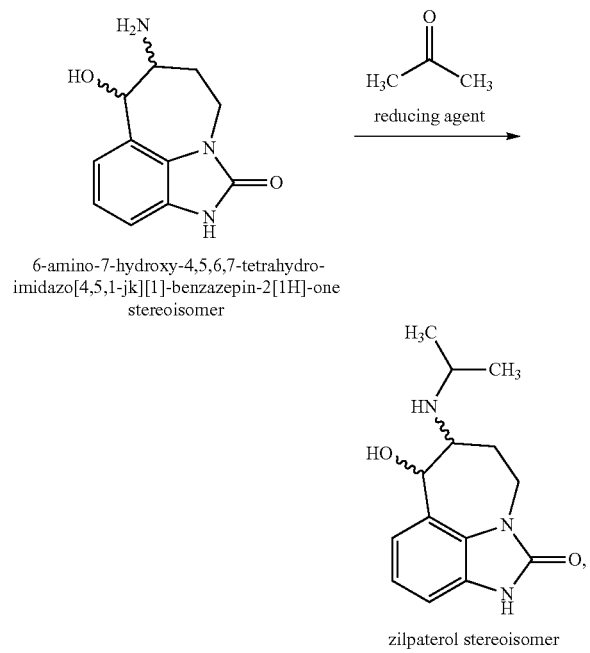

6-amino-7-hydroxy-4,5,6,7-tetrahydro-imidazo[4,5,1-jk][1]-benzazepin-2[1H]-one stereoisomer zilpaterol stereoisomer wherein the wavy lines represent a specific stereo configuration of the corresponding substituents. The reducing agent may, for example, be an alkali metal borohydride (e.g., sodium triacetoxyborohydride) or alkali metal cyanoborohydride (e.g., sodium cyanoborohydride). In this instance, the reaction preferably is conducted in a solvent. Various solvents (or combinations of solvents) may be used, such as, for example, methanol. The reaction temperature may vary widely. In general, the reaction temperature is at least about 0° C., and no greater than the boiling temperature of the solvent. In some embodiments, for example, the reaction temperature is from about zero to about 25° C. during at least a portion (and, more preferably, essentially all, or all) of the reaction. The reaction may be conducted at atmospheric pressure, less than atmospheric pressure, or greater than atmospheric pressure. Typically, however, it is conducted at about atmospheric pressure.

It should be recognized that this invention further encompasses embodiments wherein the hydrogenation reagent comprises a salt of 4,5-dihydro-imidazo[4,5,1-jk][1]benzazepin-2,6,7[1H]-trione-6-oxime, the hydrogenation product comprises (or is converted into) a salt of the 6-amino-7-hydroxy-4,5,6,7-tetrahydro-imidazo[4,5,1-jk][1]-benzazepin-2[1H]-one stereoisomer, and/or the zilpaterol product comprises (or is converted into) a zilpaterol salt.

Salts may be, for example, base or acid addition salts. In general, an acid addition salt can be prepared using various inorganic or organic acids, and a base addition salt can typically be prepared using various inorganic bases. Such salts can typically be formed by, for example, mixing a free base compound with an acid or mixing a free acid compound with a base using, for example, various methods known in the art. A salt may be advantageous due to one or more of its chemical or physical properties, such as stability in differing temperatures and humidities, or a desirable solubility in water, oil, or other solvent. In some instances, a salt of a compound also may be used as an aid in the isolation or purification of the desired stereoisomer. In some embodiments (particularly where the salt is intended for administration to an animal, or is a reagent for use in making a compound or salt intended for administration to an animal), the salt is pharmaceutically acceptable. The term "pharmaceutically acceptable" is used to characterize the salt as being appropriate for use in a pharmaceutical product. In general, a pharmaceutically acceptable salt has one or more benefits that outweigh any deleterious effect that the salt may have.

Examples of inorganic acids that typically may be used to form acid addition salts include hydrochloric, hydrobromic, hydroiodic, nitric, carbonic, sulfuric, and phosphoric acid. Examples of organic acids include, for example, aliphatic, cycloaliphatic, aromatic, araliphatic, heterocyclic, carboxylic, and sulfonic classes of organic acids. Specific examples of organic salts include cholate, sorbate, laurate, acetate, trifluoroacetate, formate, propionate, succinate, glycolate, gluconate, digluconate, lactate, malate, tartaric acid (and derivatives thereof, e.g., dibenzoyltartrate), citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate (and derivatives thereof), embonate (pamoate), ethanesulfonate, benzenesulfonate, pantothenate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

Examples of base addition salts may include, for example, metallic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with NaOH to form such a base addition salt.

Compositions containing the zilpaterol stereoisomer prepared in accordance with this invention (particularly the 6R,7R stereoisomer) may generally be used, for example, to increase the rate of weight gain, improve feed efficiency, and/or increase carcass leanness in livestock, poultry, and/or fish. Contemplated benefits of using a stereoisomer composition prepared in accordance with this invention over racemic zilpaterol include, for example, greater efficacy, greater selectivity, improved handling characteristics, fewer side effects, lower drug tissue concentrations, and/or the ability to eliminate another stereoisomer having adverse side effects.

Typically, the stereoisomer composition is administered orally. In some embodiments, the composition is added to the intended recipient animal's drinking water. In other embodiments, the stereoisomer is added to the intended recipient's feed, either directly or as part of a premix. Suitable oral dosage forms for such embodiments include, for example, solid dosage forms (e.g., tablets, hard or soft capsules, granules, powders, etc.), pastes, and liquid dosage forms (e.g., solutions, suspensions, emulsions, syrups, etc.). These dosage forms optionally comprise one or more suitable excipients. Such excipients generally include, for example, sweetening agents, flavoring agents, coloring agents, preservative agents, inert diluents (e.g., calcium carbonate, sodium carbonate, lactose, calcium phosphate, sodium phosphate, or kaolin), granulating and disintegrating agents (e.g., corn starch or alginic acid), binding agents (e.g., gelatin, acacia, or carboxymethyl cellulose), and lubricating agents (e.g., magnesium stearate, stearic acid, or talc). Liquid compositions will generally comprise a solvent. The solvent preferably has sufficient chemical properties and quantity to keep the stereoisomer solubilized at temperatures at the normal storage temperature for the composition. In some instances, it may be desirable for the compositions to comprise one or more preservatives. The presence of a preservative may, for example, allow for the compositions to be stored over a greater amount of time.

In some embodiments, the zilpaterol stereoisomer is in the form of particles adhered to a support, which, in turn, is fed to the intended recipient animal. The supported stereoisomer may be incorporated into the intended recipient's feed, either directly or as part of a premix. Contemplated supports include, for example, insert supports, such as calcium carbonate, limestone, oyster shell flour, talc, soybean hulls, soybean meal, soybean feed, soybean mill run, wheat middlings, rice hulls, corn meal, corn germ meal, corn gluten, starch, sucrose, and lactose. Particularly contemplated supports include corn cob supports, such as the support discussed in U.S. Pat. No. 5,731,028. In some embodiments employing a corn cob support, the size of the support is from about 300 to about 800 μm. Preferably, the zilpaterol stereoisomer particles that are adhered to the support have a particle size that is less than the size of the support. Thus, for example, in some embodiments in which the support is from about 300 to about 800 μm, the stereoisomer particles (or at least about 95% of the stereoisomer particles) are less than about 250 μm. In some embodiments, the size of the majority of the stereoisomer particles is from about 50 to about 200 μm. To avoid generating dust when making the supported stereoisomer, it is preferred to avoid using extremely small stereoisomer particles. In some embodiments, for example, the stereoisomer particle size distribution is such that less than about 5% of the stereoisomer particles have a particle size of less than about 15 μm. The methods discussed in, for example, U.S. Pat. No. 5,731,028 (incorporated by reference into this patent) for making a specific size distribution of crystalline racemic trans zilpaterol may generally be applied when making crystals of the negative trans stereoisomer having the above-described size distributions.

To the extent the composition is incorporated into feed, the feed mixture will vary depending on, for example, the type (e.g., species and breed), age, weight, activity, and condition of the intended recipient. For bovine and swine, various feeds are well known in the art, and often comprise cereals; sugars; grains; arachidic, tournsole, and soybean press cake; flours of animal origin, such as fish flour; amino acids; mineral salts; vitamins; antioxidants; etc. In general, the stereoisomer composition can be incorporated into any feed that is available and used for the intended recipient animal.

It is contemplated that the stereoisomer composition may be administered via non-oral routes, such as rectally, via inhalation (e.g., via a mist or aerosol), transdermally (e.g., via a transdermal patch), or parenterally (e.g., subcutaneous injection, intravenous injection, intramuscular injection, implanted device, partially implanted device etc.). In some particular embodiments, the composition is administered via an implant, such as a subcutaneous implant. For administration to bovine or swine animals, for example, the composition may be administered in the form of an implant behind the ear or baleen.

In general, the stereoisomer composition is administered in a dosage form that provides an effective amount of the stereoisomer. This is particularly true where the stereoisomer is the only active ingredient in the composition. To the extent the stereoisomer is administered with another active ingredient(s), the dosage preferably comprises an amount of the stereoisomer that, together with the amount of other active ingredient(s), constitutes an effective amount. In the context of the stereoisomer, an "effective amount" is an amount sufficient to increase the rate of weight gain, improve feed efficiency, and/or increase carcass leanness in the intended recipient (typically livestock, poultry, and/or fish).

When the composition is orally administered, it is typically preferred to use a daily dosage form. The preferred total daily dose of the stereoisomer is typically greater than about 0.01 mg/kg (i.e., milligram of stereoisomer per kilogram body weight), particularly for bovine and swine animals. In some such embodiments, the daily dose is from about 0.01 to about 50 mg/kg, from about 0.01 to about 10 mg/kg, from about 0.05 to about 2 mg/kg, from about 0.05 to about 1, or from about 0.05 to about 0.2 mg/kg. In some embodiments where the stereoisomer is administered in the recipient animal's feed, the concentration of the stereoisomer in the feed (on a 90% dry matter basis) is at least about 0.01 ppm (by weight). For bovine animals, the stereoisomer concentration is preferably no greater than about 75 ppm (by weight). In some embodiments, for example, the stereoisomer concentration is no greater than about 38 ppm, from about 0.5 to about 20 ppm, from about 3 to about 8 ppm, or from about 3.7 to about 7.5 ppm (by weight). For swine animals, the stereoisomer concentration is preferably no greater than about 45 ppm (by weight). In some such embodiments, for example, the concentration is no greater than about 23 ppm, from about 0.5 to about 20 ppm, from about 2 to about 5 ppm, or from about 2.2 to about 4.5 ppm (by weight).

Although single oral daily doses are typically preferred, it is contemplated that shorter or longer periods between doses can be used, depending on, for example, the recipient's metabolism of the stereoisomer. It is contemplated that smaller doses may be administered two or more times per day to achieve the desired total daily dose. Such multiple doses per day may, in some instances, be used to increase the total oral daily dose, if desired.

When administered via a subcutaneous implant, the preferred total daily dose of the stereoisomer is typically greater than about 0.05 mg/kg (i.e., milligram of stereoisomer per kilogram body weight), particularly for bovine and swine animals. In some such embodiments, the daily dose is from about 0.1 to about 0.25 mg/kg.

If the stereoisomer composition is administered parenterally via an injection, the concentration of the stereoisomer in the dosage form preferably is sufficient to provide the desired therapeutically effective amount of the stereoisomer in a volume that is acceptable for parenteral administration. As with oral feeding, an injection dosage form may be administered once per day, although it is contemplated that shorter or longer periods between doses also could be used.

Factors affecting the preferred dosage regimen may include, for example, the type (e.g., species and breed), age, size, sex, diet, activity, and condition of the intended recipient; the type of administration used (e.g., oral via feed, oral via drinking water, subcutaneous implant, other parenteral route, etc.); pharmacological considerations, such as the activity, efficacy, pharmacokinetic, and toxicology profiles of the particular composition administered; and whether the stereoisomer is being administered as part of a combination of active ingredients. Thus, the preferred amount of the stereoisomer can vary, and, therefore, can deviate from the typical dosages set forth above. Determining such dosage adjustments is generally within the skill of those in the art.

It is contemplated that the stereoisomer composition may be administered to the intended recipient a single time. In general, however, the composition is administered over time. In some embodiments where the animal recipient is a livestock animal, for example, the stereoisomer is administered daily for at least about 2 days, more typically daily for from about 10 to about 60 days, and still more typically daily for from about 20 to about 40 days. In some particular embodiments, the composition is administered daily for at least about the last 2 days of the finishing period. In some such embodiments, it is administered daily for from about the last 10 to about the last 60 days of the finishing period, or from about the last 20 to about the last 40 days of the finishing period. The term "finishing period" refers to the later stage of the growing period for an animal. During this period, livestock animals are typically confined in a feedlot. In some embodiments where the livestock animal is a bovine animal, this period lasts for from about 90 to about 225 days, and depends on, for example, the starting body weight of the animal. There is typically a withdrawal period following the finishing period in which no zilpaterol stereoisomer is administered. The length of this withdrawal period may depend on, for example, the type (e.g., species and breed), age, weight, activity, and condition of the recipient animal, as well as the maximum acceptable stereoisomer residue concentration in the meat of the animal.

EXAMPLES

The following examples are merely illustrative of embodiments of the invention, and not limiting to the remainder of this disclosure in any way.

Example 1

Hydrogenation of 4,5-dihydro-imidazo[4,5,1-jk][1]benzazepin-2,6,7[1H]-trione-6-oxime to selectively form a stereoisomer of 6-amino-7-hydroxy-4,5,6,7-tetrahydro-imidazo[4,5,1-jk][1]-benzazepin-2[1H]-one using an Rh(COD)LigandBF$_4$ catalyst

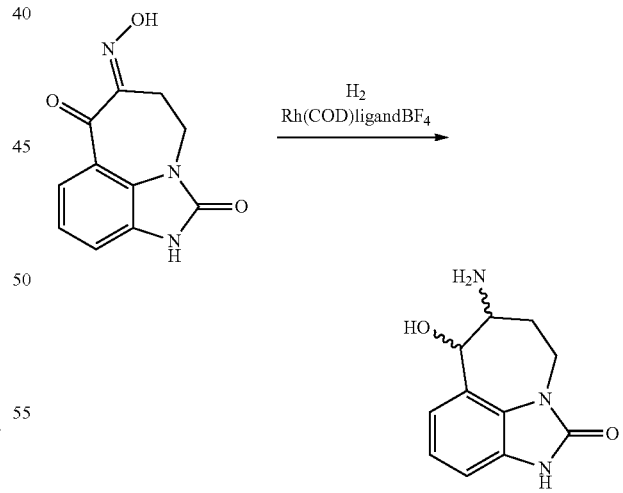

Applicants have analyzed several catalysts consisting of Rh(COD)LigandBF$_4$ for enantioselective hydrogenation of 4,5-dihydro-imidazo[4,5,1-jk][1]benzazepin-2,6,7[1H]-trione-6-oxime.

To prepare each catalyst, a ligand (0.002 mmol) and Rh(COD)$_2$BF$_4$ (0.002 mmol) were dissolved under argon in dichloromethane (0.1 ml). The resulting mixture was stirred at room temperature for 10 min.

In preparation for the hydrogenation, a substrate suspension was prepared by suspending 4,5-dihydro-imidazo[4,5,1-jk][1]benzazepin-2,6,7[1H]-trione-6-oxime (0.1 mmol) under argon in solvent (0.5 ml). In instances when an additive (i.e., an acid or base) was used, the additive (0.1 mmol) was added to the suspension at this point.

To perform each hydrogenation, the catalyst mixture was combined with the substrate suspension, and the resulting mixture was introduced into an autoclave. The autoclave was purged with $H_2$. The pressure was adjusted to 40-50 bar, and the temperature was adjusted to 35-40° C. The pressure and temperature were then maintained at those levels for 20 hr. After cooling and releasing the pressure, a sample of the mixture (0.1 ml) was collected for analysis.

To analyze a sample, approximately 25 mg of Deloxane® (a metal scavenger) was added to the sample, and the resulting suspension was stirred at 50° C. for 10 min. Afterward, the suspension was filtered through paper and diluted with 2.5 M NaOH (0.05 ml), acetonitrile (0.5 ml), and water (0.5 ml; containing 0.1% formic acid). The resulting mixtures were analyzed using HPLC.

Applicants tested numerous ligands using this procedure. Table 1 includes results that applicants perceive to be the best results under the reaction conditions.

TABLE 1

Best Results from Enantioselective Hydrogenation of 4,5-dihydro-imidazo[4,5,l-jk][1]benzazepin-2,6,7[1H]-trione-6-oxime Using an Rh(COD)LigandBF$_4$ Catalyst

| Ligand | Solvent | Acid or Base | H$_2$ Pressure (bar) | Temp (° C.) | Conversion (%) | Trans/cis | ee trans (%) | ee cis (%) |
|---|---|---|---|---|---|---|---|---|
| Formula (A-1) | methanol | none | 40 | 40 | 95 | 127.9 | −78 | −68 |
| Formula (A-1) | methanol | none | 50 | 40 | 100 | 76.9 | −91 | 8 |
| Formula (A-1) | methanol/H$_2$O (10:1 (vol)) | none | 50 | 40 | 95 | 82.3 | −93 | 6 |
| Formula (A-1) | methanol | CF$_3$CO$_2$H | 50 | 40 | 90 | 15.7 | −64 | 0 |
| Formula (A-1) | methanol/H$_2$O (10:1 (vol)) | CF$_3$CO$_2$H | 50 | 40 | 77 | 25.1 | −81 | 54 |
| Formula (A-2) | methanol | none | 40 | 40 | 82 | 26.2 | −22 | −13 |
| Formula (A-2) | methanol | none | 50 | 40 | 100 | 19.2 | −26 | 53 |
| Formula (A-2) | methanol/H$_2$O (10:1 (vol)) | none | 50 | 40 | 100 | 18.2 | −26 | 61 |
| Formula (A-2) | methanol | CF$_3$CO$_2$H | 50 | 40 | 99 | 25.6 | −32 | 52 |
| Formula (A-2) | methanol/H$_2$O (10:1 (vol)) | CF$_3$CO$_2$H | 50 | 40 | 100 | 24.2 | −33 | 60 |
| Formula (A-2) | isopropyl alcohol | CF$_3$CO$_2$H | 50 | 40 | 81 | 11734.2 | −68 | 0 |
| Formula (A-4) | methanol | CF$_3$CO$_2$H | 50 | 40 | 98 | 58.9 | −44 | 36 |
| Formula (A-4) | ethyl acetate | CF$_3$CO$_2$H | 50 | 40 | 83 | 51.3 | 0 | 0 |
| Formula (A-4) | methanol | none | 50 | 40 | 99 | 23.5 | −37 | 35 |
| Formula (A-4) | methanol/H$_2$O (10:1 (vol)) | none | 50 | 40 | 92 | 38.9 | −38 | 21 |
| Formula (B-1) | methanol | none | 50 | 40 | 80 | 16.4 | 65 | 50 |
| Formula (B-1) | methanol | CF$_3$CO$_2$H | 50 | 40 | 100 | 24.0 | 71 | 50 |
| Formula (B-1) | methanol/H$_2$O (10:1 (vol)) | CF$_3$CO$_2$H | 50 | 40 | 84 | 19.1 | 52 | 77 |
| Formula (B-1) | isopropyl alcohol | CF$_3$CO$_2$H | 50 | 40 | 75 | 2003.4 | 81 | 0 |
| Formula (B-1) | ethyl acetate | CF$_3$CO$_2$H | 50 | 40 | 99 | 44.8 | 30 | 0 |
| Formula (C-1) | methanol | none | 50 | 40 | 100 | 48.1 | 24 | |
| Formula (C-1) | methanol | none | 50 | 40 | 100 | 33.3 | 26 | |
| Formula (C-1) | methanol | KOH | 50 | 40 | 100 | 2.3 | 15 | 4 |
| Formula (C-1) | methanol | KOH | 50 | 40 | 100 | 2.5 | 15 | 9 |
| Formula (C-1) | methanol | none | 50 | 35 | 91 | 133.9 | 26 | −95 |
| Formula (C-2) | methanol | none | 50 | 40 | 92 | 15.9 | −41 | 47 |
| Formula (C-2) | methanol/H$_2$O (10:1 (vol)) | none | 50 | 40 | 92 | 19.7 | −44 | 51 |
| Formula (C-3) | methanol | none | 50 | 35 | 100 | 9.9 | 34 | −56 |
| Formula (C-3) | methanol/tetrahydrofuran (1:1 (vol)) | none | 50 | 35 | 100 | 7.6 | 29 | −63 |
| Formula (C-3) | methanol | KOH | 50 | 35 | 100 | 4.2 | 29 | −21 |
| Formula (C-3) | methanol/tetrahydrofuran (1:1 (vol)) | KOH | 50 | 35 | 100 | 7.1 | 13 | −5 |
| Formula (C-3) | methanol | none | 50 | 40 | 97 | 5.4 | 42 | 28 |
| Formula (C-3) | methanol/H$_2$O (10:1 (vol)) | none | 50 | 40 | 99 | 5.6 | 41 | 26 |
| Formula (C-3) | methanol | CF$_3$CO$_2$H | 50 | 40 | 100 | 12.1 | 36 | 69 |
| Formula (C-3) | methanol/H$_2$O (10:1 (vol)) | CF$_3$CO$_2$H | 50 | 40 | 100 | 10.8 | 35 | 63 |
| Formula (C-4) | methanol | none | 50 | 40 | 70 | 5.9 | 35 | 57 |
| Formula (C-5) | methanol | CF$_3$CO$_2$H | 50 | 40 | 94 | 11.4 | 23 | 69 |
| Formula (C-5) | methanol/H$_2$O (10:1 (vol)) | CF$_3$CO$_2$H | 50 | 40 | 87 | 15.4 | 18 | 64 |
| Formula (C-10) | methanol | none | 50 | 40 | 86 | 10.1 | 38 | 77 |
| Formula (C-10) | methanol/H$_2$O (10:1 (vol)) | none | 50 | 40 | 83 | 9.5 | 42 | 79 |
| Formula (C-15) | methanol | none | 50 | 40 | 100 | 23.8 | 57 | 82 |

TABLE 1-continued

Best Results from Enantioselective Hydrogenation of
4,5-dihydro-imidazo[4,5,1-jk][1]benzazepin-2,6,7[1H]-trione-6-oxime Using an Rh(COD)LigandBF$_4$ Catalyst

| Ligand | Solvent | Acid or Base | H$_2$ Pressure (bar) | Temp (° C.) | Conversion (%) | Trans/ cis | ee trans (%) | ee cis (%) |
|---|---|---|---|---|---|---|---|---|
| Formula (C-15) | methanol/H$_2$O (10:1 (vol)) | none | 50 | 40 | 99 | 32.2 | 57 | 82 |
| Formula (C-18) | methanol | none | 40 | 40 | 96 | 6.1 | 14 | 76 |
| Formula (C-19) | methanol | none | 50 | 40 | 95 | 29.4 | 52 | 82 |
| Formula (C-19) | methanol/H$_2$O (10:1 (vol)) | none | 50 | 40 | 85 | 22.7 | 50 | 82 |
| Formula (C-19) | methanol | CF$_3$CO$_2$H | 50 | 40 | 99 | 36.2 | 41 | 82 |
| Formula (C-19) | methanol/H$_2$O (10:1 (vol)) | CF$_3$CO$_2$H | 50 | 40 | 99 | 15.7 | 18 | 82 |
| Formula (C-20) | methanol/H$_2$O (10:1 (vol)) | none | 50 | 40 | 100 | 0.8 | −7 | 28 |
| Formula (C-23) | methanol | none | 50 | 35 | 64 | 11.9 | 31 | 63 |
| Formula (C-24) | methanol | none | 50 | 40 | 98 | 30.1 | 29 | 52 |
| Formula (C-24) | methanol/H$_2$O (10:1 (vol)) | none | 50 | 40 | 97 | 433.1 | 32 | 82 |
| Formula (C-24) | methanol | CF$_3$CO$_2$H | 50 | 40 | 100 | 24.0 | 27 | 0 |
| Formula (C-24) | methanol/H$_2$O (10:1 (vol)) | CF$_3$CO$_2$H | 50 | 40 | 80 | 13.2 | −10 | 67 |
| Formula (C-24) | isopropanol | CF$_3$CO$_2$H | 50 | 40 | 93 | 5.3 | −11 | 74 |
| Formula (C-26) | methanol | none | 50 | 40 | 96 | 28.5 | 31 | 53 |
| Formula (C-26) | methanol/H$_2$O (10:1 (vol)) | none | 50 | 40 | 92 | 40.5 | 31 | 33 |
| Formula (C-26) | methanol | CF$_3$CO$_2$H | 50 | 40 | 99 | 34.6 | 25 | 0 |
| Formula (C-27) | methanol | none | 40 | 40 | 65 | | | |
| Formula (C-31) | methanol | none | 40 | 40 | 77 | 5.1 | −68 | −22 |

The enantioselectivity ("ee") equals the difference between the concentrations of two stereoisomers divided by the total concentration of the two stereoisomers (×100%). Thus, the trans enantioselectivity equals the difference between the concentrations of the two trans stereoisomers divided by the total concentration of the two trans stereoisomers (×100%):

$$ee\ trans = \frac{[\text{first trans isomer}] - [\text{second trans isomer}]}{[\text{first trans isomer}] + [\text{second trans isomer}]} \times 100\%$$

It should be noted that the selectivity of the reaction toward a particular enantiomer can generally be changed toward the other enantiomer by using the opposite optical form of the catalyst's ligand.

Example 2

Hydrogenation of 4,5-dihydro-imidazo[4,5,1-jk][1]benzazepin-2,6,7[1H]-trione-6-oxime to selectively form a stereoisomer of 6-amino-7-hydroxy-4,5,6,7-tetrahydro-imidazo[4,5,1-jk][1]-benzazepin-2[1H]-one using an RuCl$_2$Ligand(DMF)$_2$ catalyst

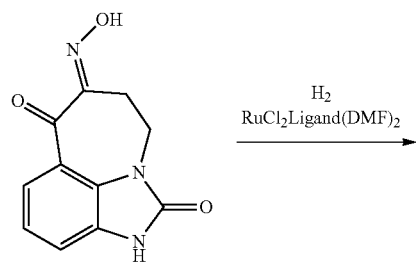

-continued

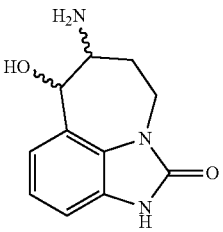

Applicants have analyzed several catalysts consisting of RuCl$_2$Ligand(DMF)$_2$ for enantioselective hydrogenation of 4,5-dihydro-imidazo[4,5,1-jk][1]benzazepin-2,6,7[1H]-trione-6-oxime.

To prepare each catalyst, a ligand (0.002 mmol) and [Ru(C$_6$H$_6$)Cl$_2$]$_2$ (0.001 mmol) were dissolved under argon in dimethylformamide (0.05 ml). The resulting mixture was stirred at 100° C. for 10 min.

In preparation for the hydrogenation, a substrate suspension was prepared by suspending 4,5-dihydro-imidazo[4,5,1-jk][1]benzazepin-2,6,7[1H]-trione-6-oxime (0.1 mmol) under argon in solvent (0.5 ml). In instances when an additive (i.e., a base) was used, the additive (0.1 mmol) was added to the suspension at this point.

To perform each hydrogenation, the catalyst mixture was combined with the substrate suspension, and the resulting mixture was introduced into an autoclave. The autoclave was purged with H$_2$. The pressure was adjusted to 20-60 bar, and the temperature was adjusted to 50-80° C. The pressure and temperature were then maintained at those levels for 20 hr. After cooling and releasing the pressure, a sample of the mixture (0.1 ml) was collected for analysis.

To analyze a sample, approximately 25 mg of Deloxane® was added to the sample, and the resulting suspension was stirred at 50° C. for 10 min. Afterward, the suspension was filtered through paper and diluted with 2.5 M NaOH (0.05 ml), acetonitrile (0.5 ml), and water (0.5 ml; containing 0.1% formic acid). The resulting mixtures were analyzed using HPLC.

Applicants tested numerous ligands using this procedure. Table 2 includes results that applicants perceive to be the best results under the reaction conditions.

TABLE 2

Best Results from Enantioselective Hydrogenation of
4,5-dihydro-imidazo[4,5,l-jk][1]benzazepin-2,6,7[1H]-trione-6-oxime Using an $RuCl_2Ligand(DMF)_2$ Catalyst

| Ligand | Solvent | Base | $H_2$ Pressure (bar) | Temp (° C.) | Conversion (%) | Trans/cis | ee trans (%) | ee cis (%) |
|---|---|---|---|---|---|---|---|---|
| Formula (C-1) | methanol | KOH | 50 | 65 | 83 | 0.9 | −15 | 30 |
| Formula (C-1) | methanol/tetrahydrofuran (1:1 (vol)) | KOH | 50 | 65 | 82 | 0.9 | −23 | 13 |
| Formula (C-2) | methanol | KOH | 40 | 70 | 78 | 0.5 | −51 | −21 |
| Formula (C-6) | methanol | KOH | 50 | 50 | 100 | 2.5 | −27 | −12 |
| Formula (C-6) | methanol/tetrahydrofuran (1:1 (vol)) | KOH | 50 | 50 | 100 | nd | nd | nd |
| Formula (C-7) | methanol/tetrahydrofuran (1:1 (vol)) | KOH | 50 | 50 | 100 | 1.0 | −23 | 1 |
| Formula (C-8) | methanol/tetrahydrofuran (1:1 (vol)) | KOH | 50 | 65 | 62 | 1.0 | −6 | 32 |
| Formula (C-9) | methanol | KOH | 50 | 50 | 94 | 3.6 | 7 | −9 |
| Formula (C-9) | methanol/tetrahydrofuran (1:1 (vol)) | KOH | 50 | 50 | 100 | 3.2 | 3 | 8 |
| Formula (C-11) | methanol | KOH | 50 | 50 | 72 | 2.1 | −6 | 5 |
| Formula (C-11) | methanol/tetrahydrofuran (1:1 (vol)) | KOH | 50 | 50 | 100 | 2.9 | −13 | −6 |
| Formula (C-12) | methanol | KOH | 50 | 50 | 100 | 1.3 | −9 | 3 |
| Formula (C-12) | methanol/tetrahydrofuran (1:1 (vol)) | KOH | 50 | 50 | 100 | 0.7 | −5 | 51 |
| Formula (C-13) | methanol | KOH | 40 | 70 | 100 | nd | nd | nd |
| Formula (C-14) | methanol | KOH | 50 | 50 | 100 | 2.3 | −20 | 10 |
| Formula (C-14) | methanol/tetrahydrofuran (1:1 (vol)) | KOH | 50 | 50 | 100 | 1.7 | −26 | 29 |
| Formula (C-16) | methanol | KOH | 50 | 50 | 84 | 1.9 | −12 | −2 |
| Formula (C-16) | methanol/tetrahydrofuran (1:1 (vol)) | KOH | 50 | 50 | 100 | 1.6 | −23 | −4 |
| Formula (C-17) | methanol | KOH | 50 | 50 | 88 | 2.8 | −13 | −1 |
| Formula (C-17) | methanol/tetrahydrofuran (1:1 (vol)) | KOH | 50 | 50 | 100 | 0.8 | −50 | 82 |
| Formula (C-21) | methanol | KOH | 50 | 50 | 100 | 1.0 | −8 | 7 |
| Formula (C-21) | methanol/tetrahydrofuran (1:1 (vol)) | KOH | 50 | 50 | 100 | 1.1 | −58 | −2 |
| Formula (C-22) | dimethylformamide | none | 60 | 80 | 100 | nd | nd | nd |
| Formula (C-25) | methanol | KOH | 50 | 65 | 89 | 0.7 | 53 | 22 |
| Formula (C-25) | methanol/tetrahydrofuran (1:1 (vol)) | KOH | 50 | 65 | 63 | 0.5 | 16 | 1 |
| Formula (C-28) | dimethylformamide | none | 60 | 80 | 100 | nd | nd | nd |
| Formula (C-28) | methanol | none | 60 | 80 | 100 | nd | nd | nd |
| Formula (C-28) | tetrahydrofuran | KOH | 60 | 70 | 100 | nd | nd | nd |
| Formula (C-28) | methanol | KOH | 20 | 70 | 100 | nd | nd | nd |
| Formula (C-28) | tetrahydrofuran | KOH | 20 | 70 | 100 | nd | nd | nd |
| Formula (C-28) | methanol | none | 50 | 70 | 100 | 4.44 | 20 | nd |
| Formula (C-28) | tetrahydrofuran | KOH | 50 | 70 | 100 | nd | nd | nd |
| Formula (C-29) | methanol | none | 40 | 70 | 100 | nd | nd | nd |
| Formula (C-30) | methanol | KOH | 50 | 50 | 100 | 1.7 | −9 | 43 |
| Formula (C-30) | methanol/tetrahydrofuran | KOH | 50 | 50 | 100 | 1.6 | −15 | 22 |
| Formula (C-31) | methanol | none | 40 | 70 | 100 | 6.7 | 25 | −4 |

"nd" means not determined.

As noted in Example 1, the selectivity of the reaction toward a particular enantiomer can generally be changed toward the enantiomer by using the opposite optical form of the catalyst's ligand.

Example 3

Synthesis of (6R,7R)-6-amino-7-hydroxy-4,5,6,7-tetrahydro-imidazo[4,5,1-jk][1]-benzazepin-2 [1H]-one

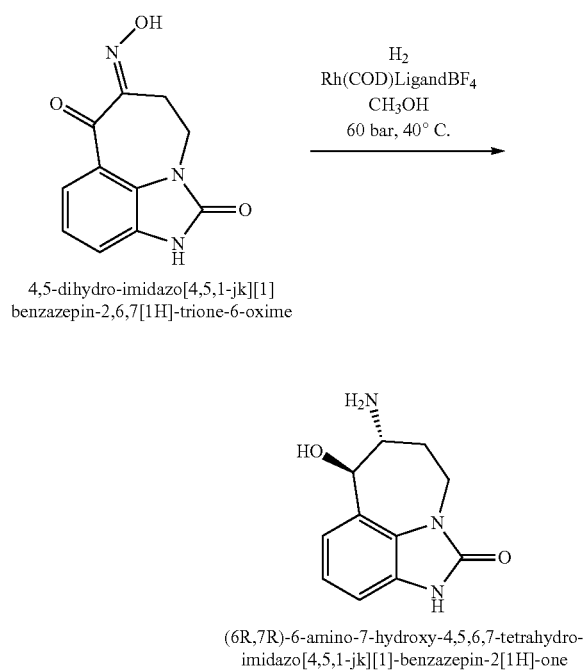

A catalyst solution was prepared by dissolving (R,R)-(+)-2,2'-bis[(S)—(N,N-dimethylamino)(phenyl)methyl]-1,1'-bis[di(3,5-dimethyl-4-methoxyphenyl)phosphino]ferrocene (52.6 mg; 0.05 mmol; identified above as Ligand Formula (A-1B)) and bis(1,5-cyclooctadiene)rhodium(I)tetrafluoroborate (20.4 mg; 0.05 mmol; also known as "Rh(COD)$_2$BF$_4$") in dichloromethane (1 ml) under argon, and then stirring the resulting mixture at room temperature for 10 min. In parallel, 4,5-dihydro-imidazo[4,5,1-jk][1]benzazepin-2,6,7[1H]-trione-6-oxime (1.15 g, 5.0 mmol) was charged into a 100 mL autoclave and suspended in 40 mL of methanol. The autoclave was purged 3 times with H$_2$ without stirring at 20 bar, and 3 times with stirring at 20 bar. Afterward, the catalyst solution, diluted with 4 ml of methanol, was charged into the autoclave. Hydrogen pressure (60 bar) was then applied, and the mixture was stirred at that pressure for 22 hr at 40° C. After cooling the mixture to room temperature and releasing the pressure, 2 g of Deloxan® THP II were added, and the resulting suspension was stirred at 55° C. for 10 min and filtered. The solvents were then removed to yield the product.

Example 4

Synthesis of the HCl salt of (6R,7R)-4,5,6,7-tetrahydro-7-hydroxy-6-(isopropylamino)imidazo[4,5,1-jk]-[1]benzazepin-2(1H)-one (i.e., trans(−) zilpaterol HCl)

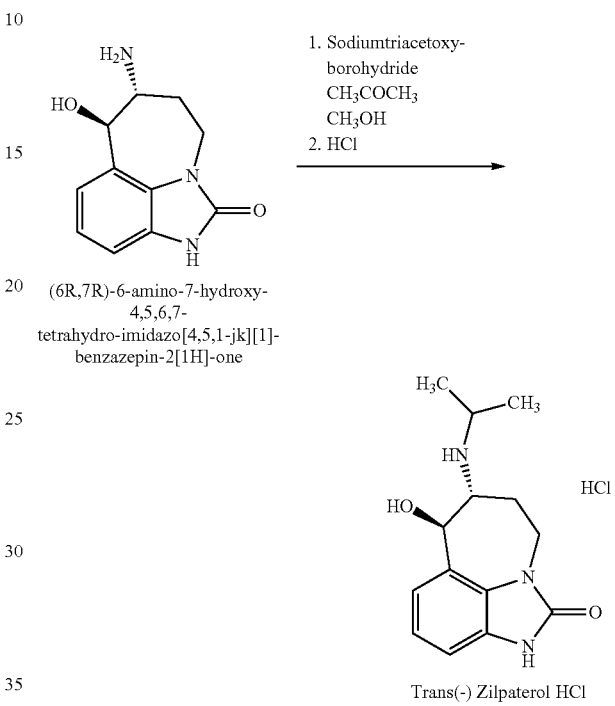

Product from Example 3 was dissolved in methanol (6 ml) and acetone (3 ml). The resulting mixture was then stirred under ice-cooling. After 10 min, sodium triacetoxyborohydride (1.2 g, 5.66 mmol) was added, and the mixture was allowed to attain room temperature. After 5 hr of stirring at this temperature, further sodium triacetoxyborohydride (0.25 g, 1.2 mmol) was added, and the mixture was stirred over night. Afterward, the volatiles were removed in vacuo, and 1 N HCl (6 ml) and water (2 ml) were added to the resulting residue. After filtration, the filtrate was freeze-dried. The resulting residue was then recrystallized from ethanol (10 mL). The solid was discarded, and the filtrate was concentrated in vacuo. The resulting residue was triturated with hot ethanol (14 mL), and the remaining solid was collected by filtration and then dried. This desired product was obtained as a solid (802 mg, 2.7 mmol, 54%, 81% ee). m.p. 173-174° C. (dec., from ethanol); [α]$_D$=−26° (c 1.0, methanol, 20° C.); ν$_{max}$/cm$^{-1}$ (neat) 3403, 2979, 2802, 2711, 1699, 1598, 1477, 1394, 1268, 1150, 1096, 1030, 782, 743, 683; δ$_H$ (400 MHz, CD$_3$OD) 1.40 (d, J=6.3 Hz, 3H), 1.45 (d, J=6.3 Hz, 3H), 2.09-2.19 (m, 1H), 2.55-2.63 (m, 1H), 3.61-3.73 (m, 2H), 3.87-3.95 (m, 1H), 4.22-4.32 (m, 1H), 5.02 (d, J=8.4 Hz, 1H), 7.05 (d, J=7.8 Hz, 1H), 7.12 (dd, J=7.8 Hz, J=7.8 Hz, 1H), 7.33 (d, J=7.8 Hz, 1H); δ$_C$ (100 MHz, CD$_3$OD) 18.8, 20.2, 28.2, 40.5, 50.4, 61.8, 71.9, 110.5, 122.1, 122.8, 122.9, 127.8, 129.9, 156.5; m/z (API-ES) 262.1 (M+H$^+$).

Example 5

First Illustration of a Contemplated Suitable Dosage Form

A tablet is prepared containing 2.5 or 5 mg of the HCl salt of Example 4, and sufficient excipient of lactose, wheat starch, treated starch, rice starch, talc, and magnesium stearate for a final weight of 100 mg.

Example 6

Second Illustration of a Contemplated Suitable Dosage Form

Granules are prepared containing 12.5 or 25 of the HCl salt of Example 4 in each daily dose of granules.

Example 7

Third Illustration of a Contemplated Suitable Dosage Form

The HCl salt of Example 4 is crystallized using the methodology discussed U.S. Pat. No. 5,731,028 for making crystalline racemic trans zilpaterol. Less than 5% of the crystals have a size of less than 15 μm, and at least 95% of the crystals have a size of less than 250 μm. A premix of the crystalline HCl salt secured to a 300-800 μm corn cob support is then obtained using the methodology discussed in European Patent 0197188 (incorporated by reference into this patent). The concentration of the HCl salt in the premix is 3% (by weight).

The words "comprise," "comprises," and "comprising" in this patent (including the claims) are to be interpreted inclusively rather than exclusively. This interpretation is intended to be the same as the interpretation that these words are given under United States patent law.

All references cited in this patent are incorporated by reference into this patent.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

What is claimed is:

1. A process for selectively making a stereoisomer of 6-amino-7-hydroxy-4,5,6,7-tetrahydro-imidazo[4,5,1-jk][1]-benzazepin-2[1H]-one or a salt thereof, the process comprising:
   reacting 4,5-dihydro-imidazo[4,5,1-jk][1]-benzazepin-2,6,7[1H]-trione-6-oxime or a salt thereof with $H_2$ in the presence of a catalyst, wherein the catalyst comprises a metal complex of at least one metal from transition group VIII with at least one ligand.

2. The process according to claim 1, wherein the metal from the transition group VIII comprises ruthenium.

3. The process according to claim 1, wherein the metal from the transition group VIII comprises rhodium.

4. The process according to claim 3, wherein the metal complex comprises Rh(1,5-cyclo-octadiene)ligandBF$_4$.

5. The process according to claim 1, wherein the ligand is selected from the group consisting of the following ligands and enantiomers thereof:

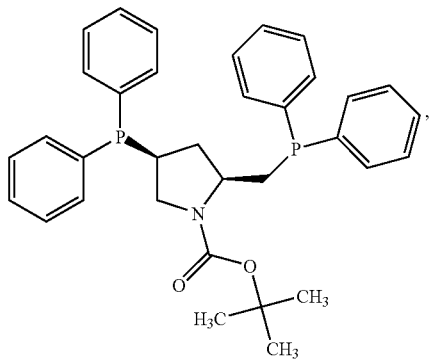

C-1

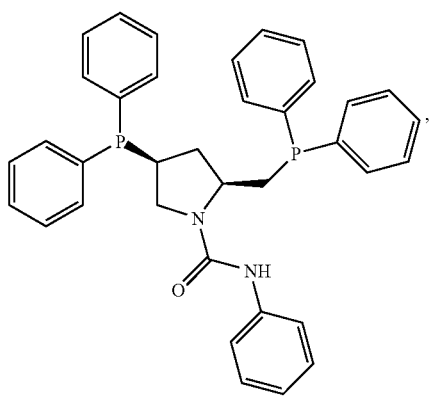

C-2

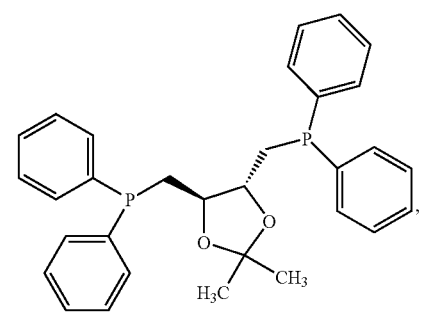

C-3

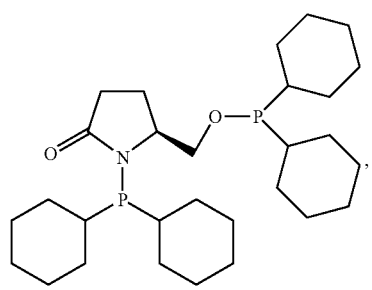

C-4

C-5
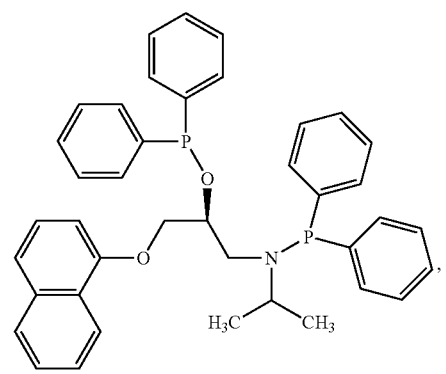
C-6
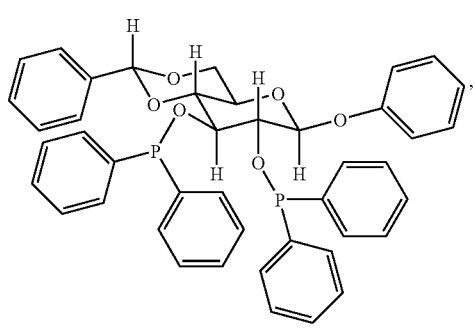
C-7
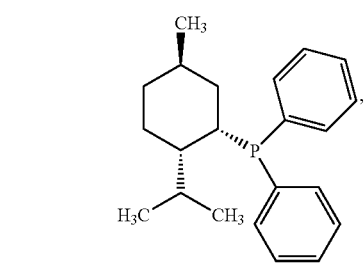
C-8
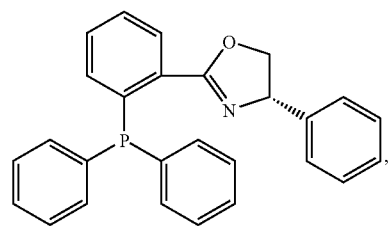
C-9
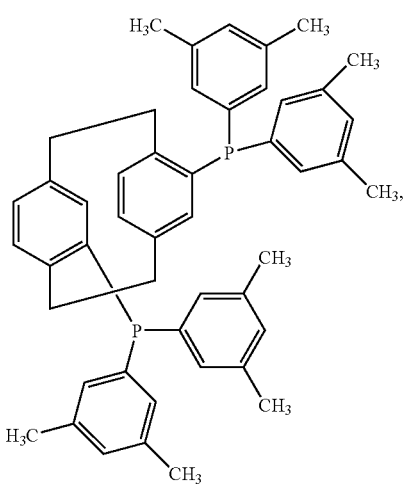
C-10
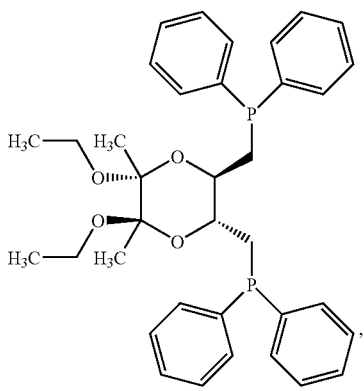
C-11
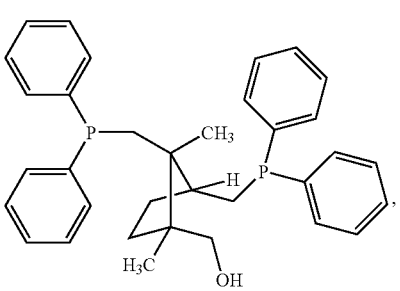
C-12
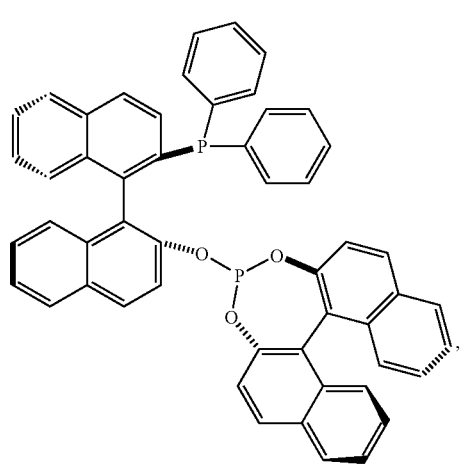
C-13
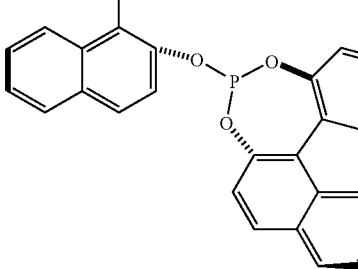
C-14
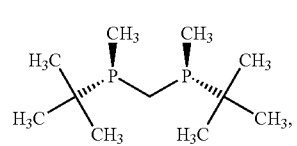

-continued
C-15
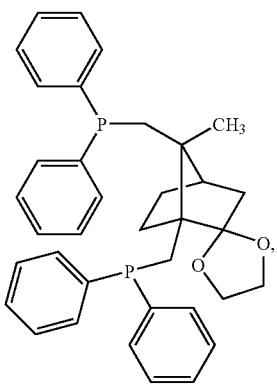
C-16
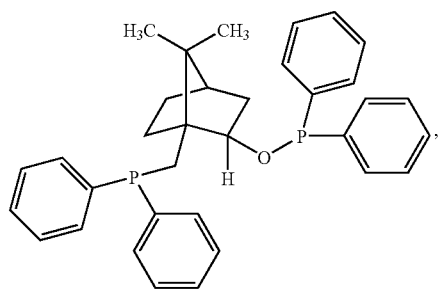
C-17
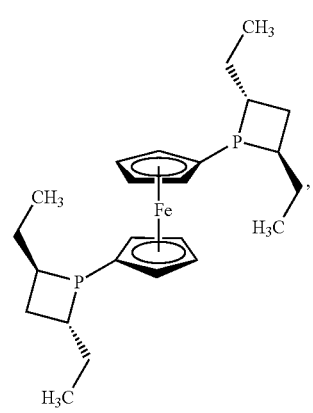
C-18
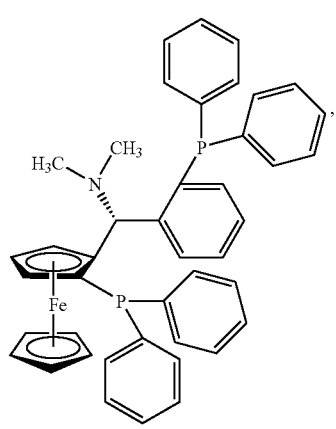
-continued
C-19
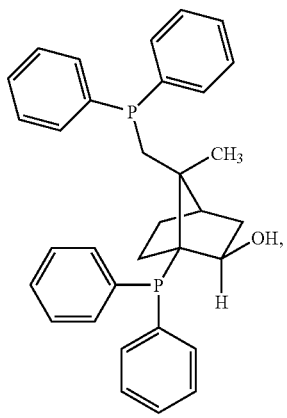
C-20
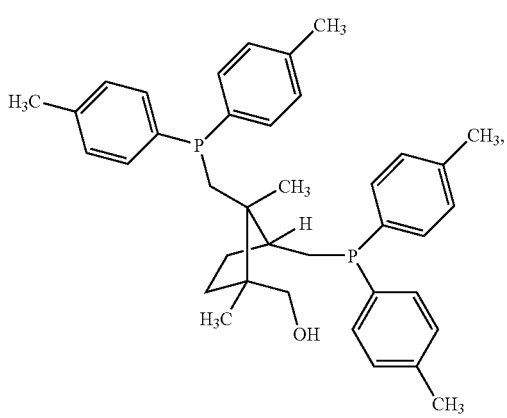
C-21
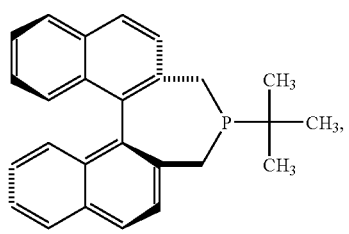
C-22
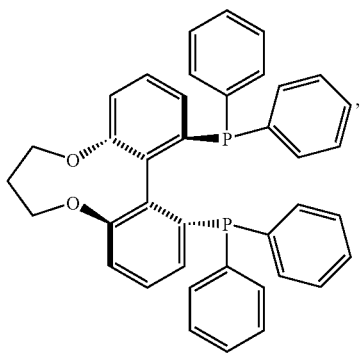

C-23
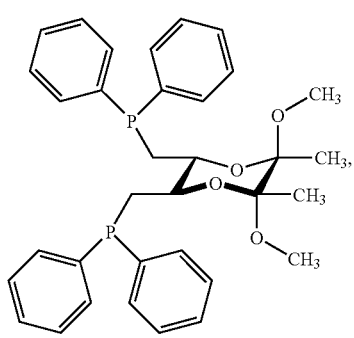
C-24
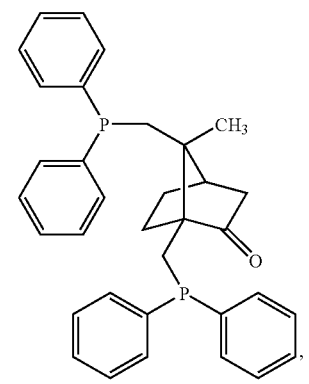
C-25
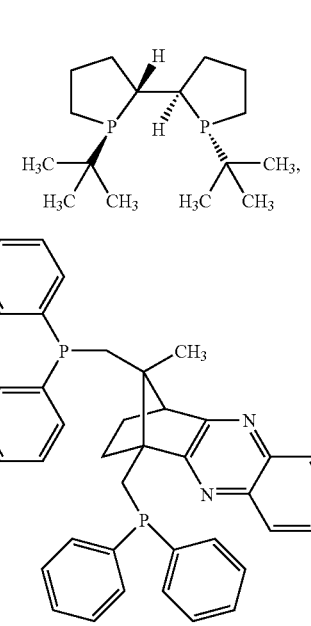
C-26
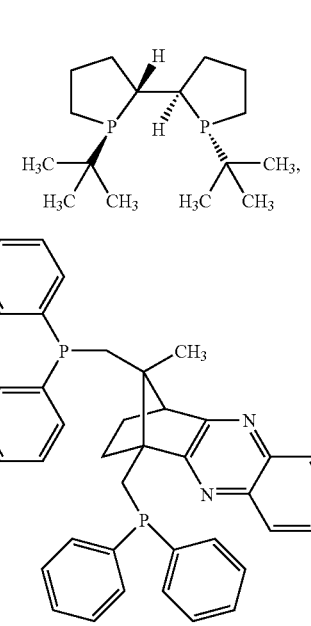
C-27
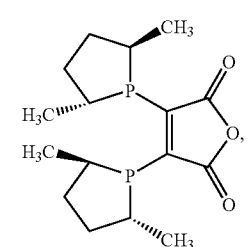
C-28
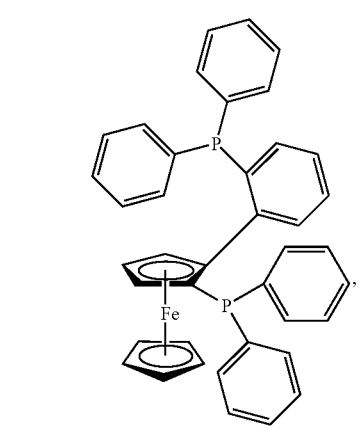
C-29
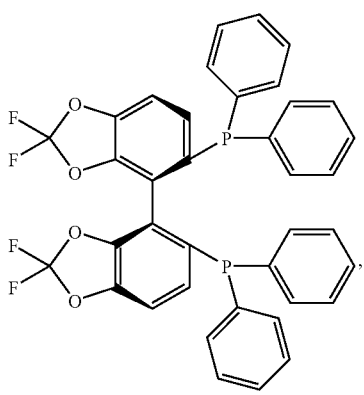
C-30
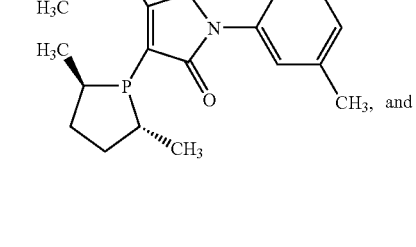
C-31
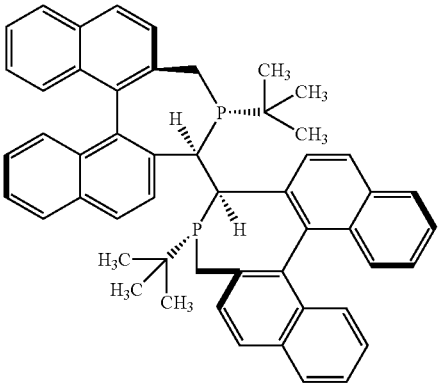
6. The process according to claim 1, wherein: the ligand corresponds in structure to Formula (A) or Formula (B):

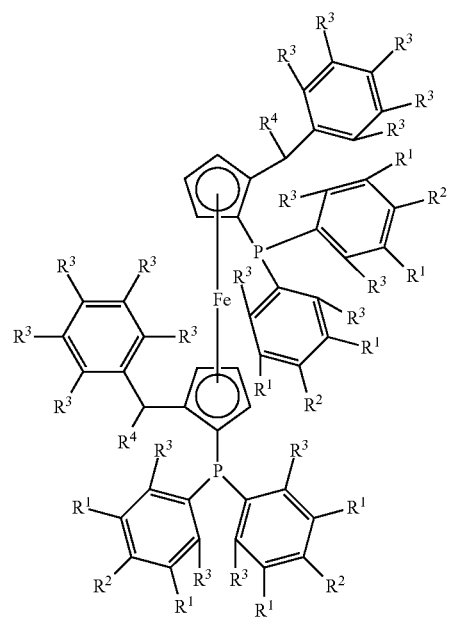

(A)

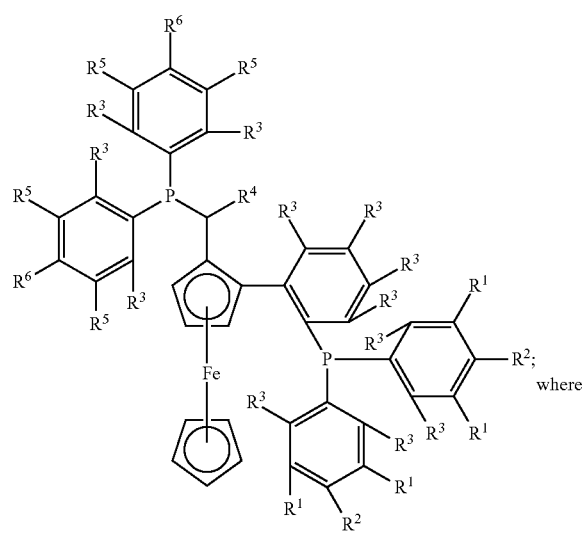

(B) where each of R¹, R², R⁵, and R⁶ is independently selected from the group consisting of hydrogen, $C_1$-$C_6$-alkyl, hydroxy, and $C_1$-$C_6$-alkoxy, wherein:
  the $C_1$-$C_6$-alkyl and $C_1$-$C_6$-alkoxy are optionally substituted by one or more halogen;
each R³ is independently selected from the group consisting of hydrogen and $C_1$-$C_6$-alkyl;
each R⁴ is independently selected from the group consisting of hydrogen, $C_1$-$C_6$-alkyl, and $NR^7R^8$; and
as to each of R⁷ and R⁸:
  each of R⁷ and R⁸ is independently selected from the group consisting of hydrogen and $C_1$-$C_6$-alkyl, or
  R⁷ and R⁸, together with the nitrogen to which they are commonly attached, form a saturated heterocycle.

7. The process according to claim 6, wherein the ligand corresponds in structure to Formula (A).

8. The process according to claim 7, wherein the ligand corresponds in structure to Formula (A-1):

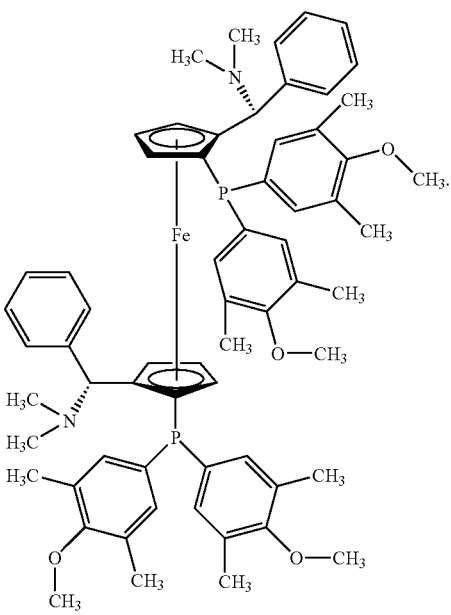

(A-1)

9. The process according to claim 7, wherein the ligand corresponds in structure to Formula (A-1B):

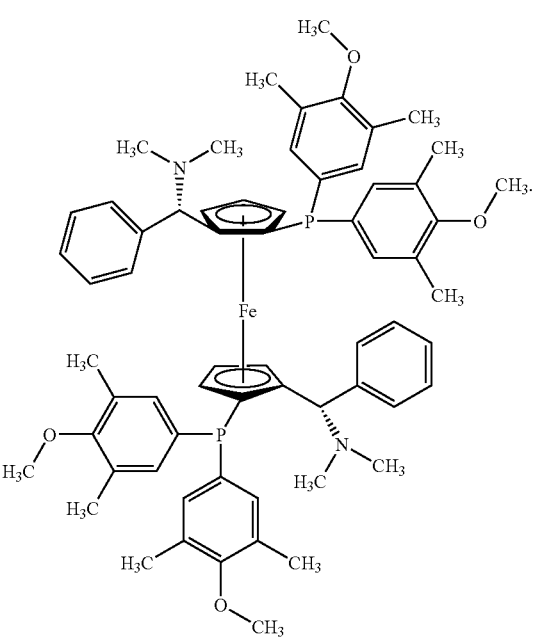

(A-1B)

10. The process according to claim 7, wherein the ligand corresponds in structure to Formula (A-2):

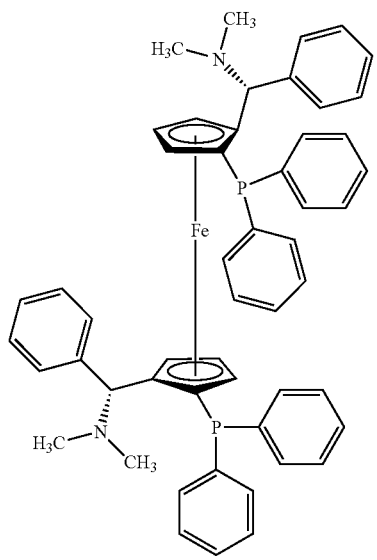

or the enantiomer thereof.

11. The process according to claim 7, wherein the ligand corresponds in structure to Formula (A-4):

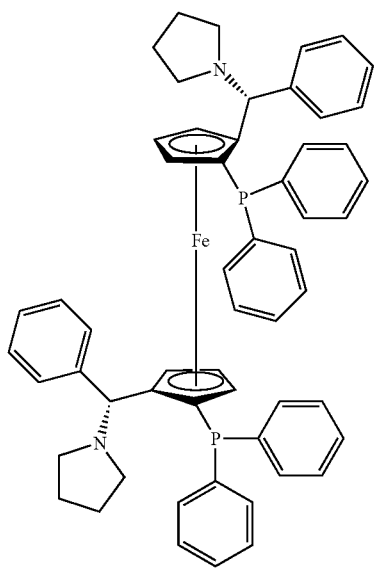

or the enantiomer thereof.

12. The process according to claim 6, wherein the ligand corresponds in structure to Formula (B).

13. The process according to claim 12, wherein the ligand corresponds in structure to Formula (B-1):

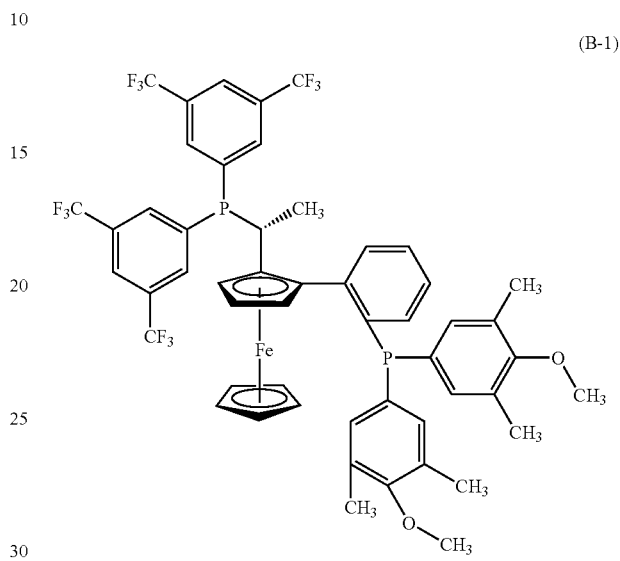

or the enantiomer thereof.

14. The process according to claim 1, wherein 4,5-dihydro-imidazo[4,5,1-jk][1]benzazepin-2,6,7[1H]-trione-6-oxime or a salt thereof is reacted with $H_2$ in the presence of a homogeneous catalyst in a solvent or solvent mixture comprising at least one solvent selected from the group consisting of methanol, water, tetrahydrofuran, isopropyl alcohol, toluene, ethyl acetate, and dimethylformamide.

15. The process according to claim 1, wherein 4,5-dihydro-imidazo[4,5,1-jk][1]benzazepin-2,6,7[1H]-trione-6-oxime or a salt thereof is reacted with $H_2$ in the presence of a base.

16. The process according to claim 1, wherein 4,5-dihydro-imidazo[4,5,1-jk][1]benzazepin-2,6,7[1H]-trione-6-oxime or a salt thereof is reacted with $H_2$ in the presence of an acid.

17. The process according to claim 1, wherein 4,5-dihydro-imidazo[4,5,1-jk][1]benzazepin-2,6,7[1H]-trione-6-oxime or a salt thereof is reacted with $H_2$ at an $H_2$ pressure that is greater than atmospheric pressure but less than or equal to about 70 bars.

18. The process according to claim 1, wherein 4,5-dihydro-imidazo[4,5,1-jk][1]benzazepin-2,6,7[1H]-trione-6-oxime or a salt thereof is reacted with $H_2$ in the presence of a solvent at a temperature that is at least about 20° C. but less than or equal to the boiling point of the solvent at the pressure in which the reaction is conducted.

19. The process according to claim 1, wherein the stereoisomer corresponds in structure to Formula (IIa):

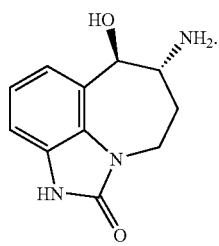

(IIa)

20. A process for selectively making a stereoisomer of zilpaterol or a salt thereof, wherein the process comprises:

reacting 4,5-dihydro-imidazo[4,5,1-jk][1]benzazepin-2,6,7[1H]-trione-6-oxime with H₂ in the presence of a catalyst comprising a metal complex of at least one metal from transition group VIII with at least one ligand, to form 6-amino-7-hydroxy-4,5,6,7-tetrahydro-imidazo[4,5,1-jk][1]-benzazepin-2[1H]-one or a salt thereof; and converting the 6-amino-7-hydroxy-4,5,6,7-tetrahydro-imidazo[4,5,1-jk][1]-benzazepin-2[1H]-one into the stereoisomer of zilpaterol.

21. The process according to claim 20, wherein the stereoisomer of zilpaterol corresponds in structure to Formula (IIIa):

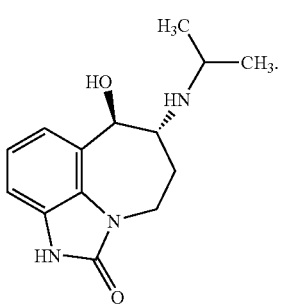

(IIIa)

22. The process according to claim 21, wherein the process comprises reacting the 6-amino-7-hydroxy-4,5,6,7-tetrahydro-imidazo[4,5,1-jk][1]-benzazepin-2[1H]-one with acetone in the presence of a reducing agent.

23. The process according to claim 22, wherein the reducing agent comprises sodium triacetoxyborohydride.

24. The process according to claim 20, wherein:
the metal complex comprises Rh(1,5-cyclo-octadiene)ligandBF₄;
the ligand corresponds in structure to Formula (A-1B):

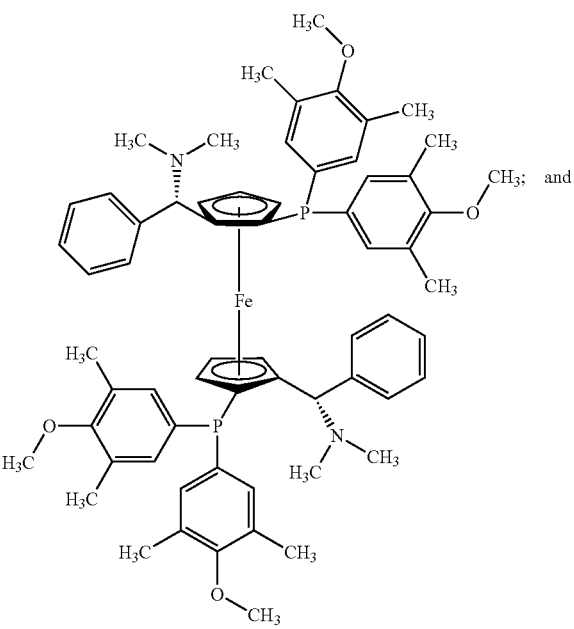

(A-1B)

the 4,5-dihydro-imidazo[4,5,1-jk][1]benzazepin-2,6,7[1H]-trione-6-oxime is reacted with the H₂:
in the presence of a solvent comprising methanol,
at a temperature of from about 25 to about 45° C.,
at an H₂ pressure of from about 20 to about 60 bars, and
in a reactor charged with 4,5-dihydro-imidazo[4,5,1-jk][1]benzazepin-2,6,7[1H]-trione-6-oxime and homogeneous catalyst such that the molar ratio of the charged 4,5-dihydro-imidazo[4,5,1-jk][1]benzazepin-2,6,7[1H]-trione-6-oxime to the charged catalyst is from about 50:1 to about 200:1.

25. A method for increasing an animal's rate of weight gain, improving an animal's feed efficiency, and/or increasing an animal's carcass leanness, wherein the method comprises:
administering to the animal an effective amount of the zilpaterol stereoisomer or salt thereof prepared by the process according to claim 20.

26. The method according to claim 25, wherein the stereoisomer corresponds in structure to Formula (IIIa):

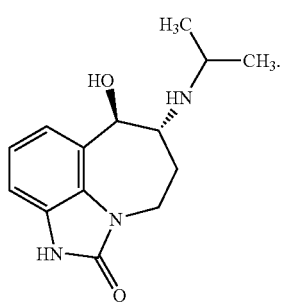

(IIIa)

27. A method for increasing an animal's rate of weight gain, improving an animal's feed efficiency, and/or increasing an animal's carcass leanness, wherein the method comprises:

administering to the animal an effective amount of the zilpaterol stereoisomer or salt thereof prepared by the process of claim 20, wherein the stereoisomer of zilpaterol corresponds in structure to Formula (IIIa):

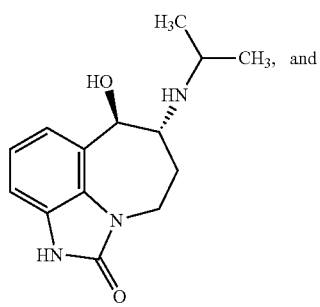

(IIIa)

wherein the process utilized for preparing the zilpaterol stereoisomer or salt thereof comprises reacting the 6-amino-7-hydroxy-4,5,6,7-tetrahydro-imidazo[4,5,1-jk][1]-benzazepin-2[1H]-one with acetone in the presence of a reducing agent.

28. The method according to claim 27, wherein the reducing agent comprises sodium triacetoxyborohydride.

29. The method according to claim 28, wherein the metal complex utilized in the process for preparing the zilpaterol stereoisomer or salt thereof comprises Rh(1,5-cyclo-octadiene)ligandBF$_4$;

the ligand corresponds in structure to Formula (A-1B):

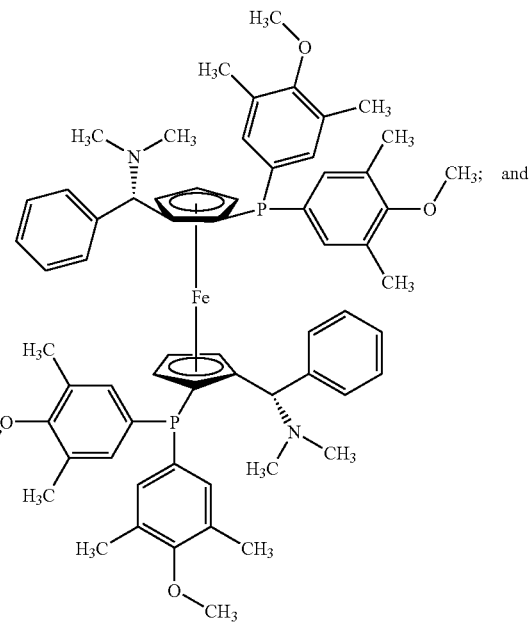

(A-1B)

the 4,5-dihydro-imidazo[4,5,1-jk][1]benzazepin-2,6,7 [1H]-trione-6-oxime is reacted with the H$_2$:

in the presence of a solvent comprising methanol, at a temperature of from about 25 to about 45° C., at an H$_2$ pressure of from about 20 to about 60 bars, and in a reactor charged with 4,5-dihydro-imidazo[4,5,1-jk] [1]benzazepin-2,6,7[1H]-trione-6-oxime and homogeneous catalyst such that the molar ratio of the charged 4,5-dihydro-imidazo[4,5,1-jk][1]benzazepin-2,6,7[1H]-trione-6-oxime to the charged catalyst is from about 50:1 to about 200:1.

* * * * *

UNITED STATES PATENT AND TRADEMARK OFFICE
CERTIFICATE OF CORRECTION

PATENT NO. : 8,629,134 B2  Page 1 of 1
APPLICATION NO. : 12/525222
DATED : January 14, 2014
INVENTOR(S) : Almena-Perea et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 547 days.

Signed and Sealed this
Twenty-second Day of September, 2015

Michelle K. Lee
*Director of the United States Patent and Trademark Office*